(12) United States Patent
McDevitt et al.

(10) Patent No.: US 6,733,506 B1
(45) Date of Patent: May 11, 2004

(54) APPARATUS AND METHOD FOR ATTACHING SOFT TISSUE TO BONE

(75) Inventors: Dennis McDevitt, Upton, MA (US); Vince Novak, Groton, MA (US); Geary H. Munroe, Norton, MA (US); Thomas E. Borg, Walpole, MA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/714,549

(22) Filed: Nov. 16, 2000

(51) Int. Cl.[7] ............................................... A61B 17/84
(52) U.S. Cl. ....................................... 606/104; 606/232
(58) Field of Search ............................. 606/72–75, 104, 606/139, 144, 232; 411/15, 32, 44, 57.1, 60.1, 80.1, 80.2, 80.5, 80.6, 493, 29, 30, 41

(56) References Cited

U.S. PATENT DOCUMENTS

| | | | | |
|---|---|---|---|---|
| 5,209,753 A | * | 5/1993 | Biedermann et al. | 606/72 |
| 5,480,403 A | * | 1/1996 | Lee et al. | 606/72 |
| 5,522,817 A | * | 6/1996 | Sander et al. | 606/72 |
| 5,601,558 A | * | 2/1997 | Torrie et al. | 606/72 |
| 5,725,541 A | * | 3/1998 | Anspach et al. | 606/151 |
| 5,782,865 A | * | 7/1998 | Grotz | 606/232 |
| 5,928,244 A | * | 7/1999 | Tovey et al. | 606/104 |
| 5,957,953 A | * | 9/1999 | DiPoto et al. | 606/232 |
| 5,968,044 A | * | 10/1999 | Nicholson et al. | 606/72 |
| 6,319,252 B1 | * | 11/2001 | McDevitt et al. | 606/60 |
| 2002/0115999 A1 | * | 8/2002 | McDevitt et al. | 606/60 |

* cited by examiner

Primary Examiner—John J. Wilson
Assistant Examiner—Michael B. Priddy
(74) Attorney, Agent, or Firm—Pandiscio & Pandiscio

(57) ABSTRACT

An apparatus for attaching soft tissue to bone.

78 Claims, 24 Drawing Sheets

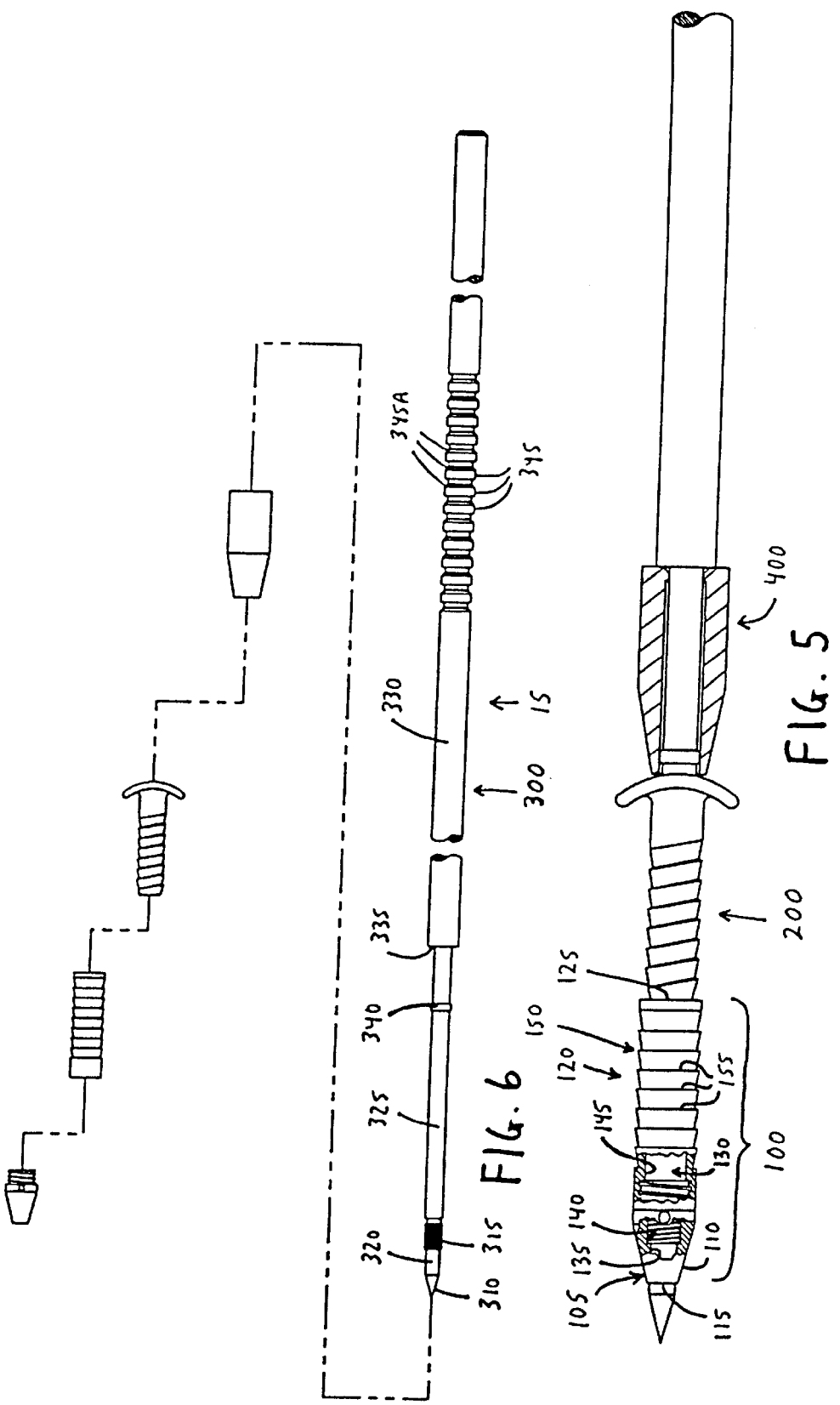

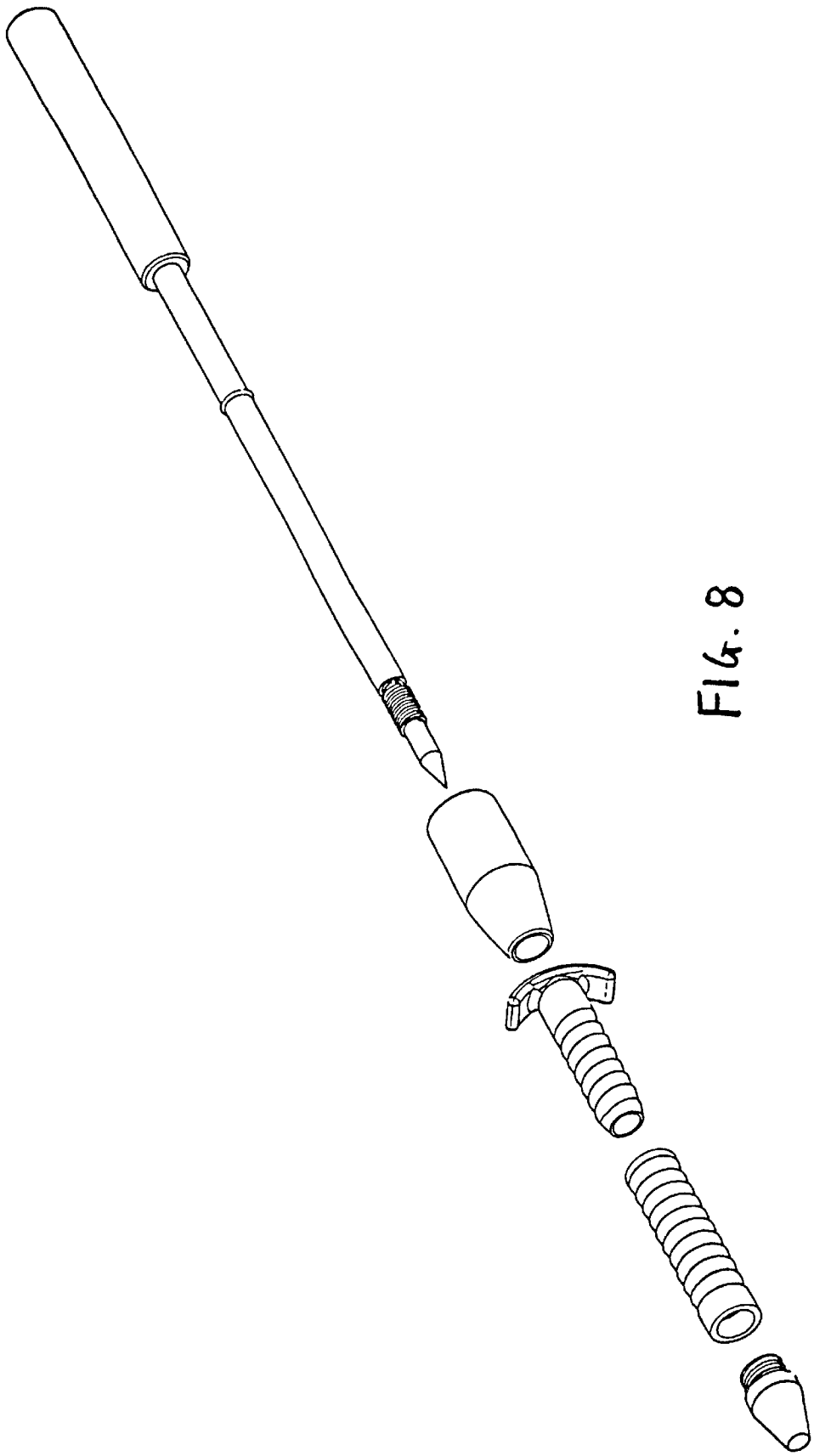

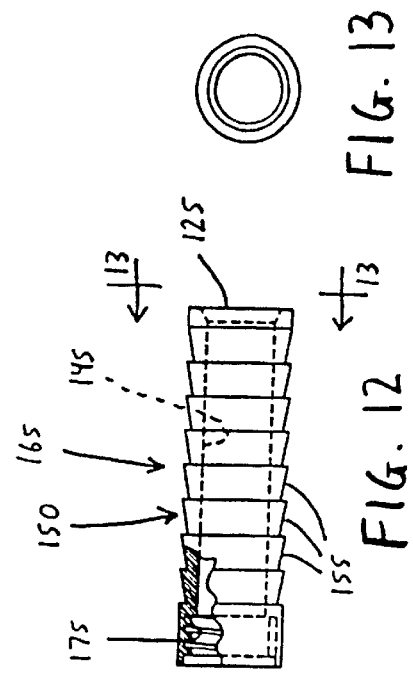
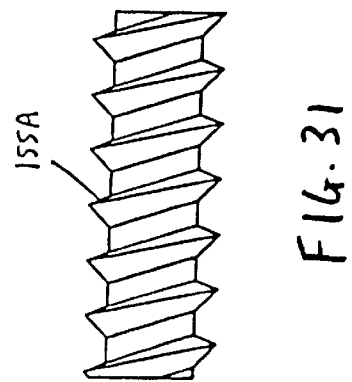
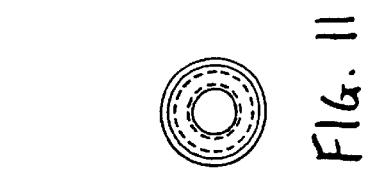
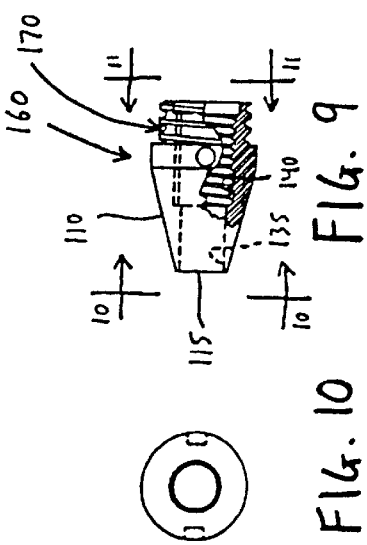
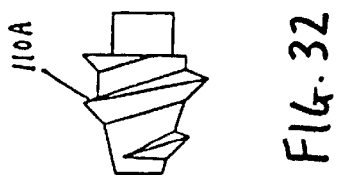

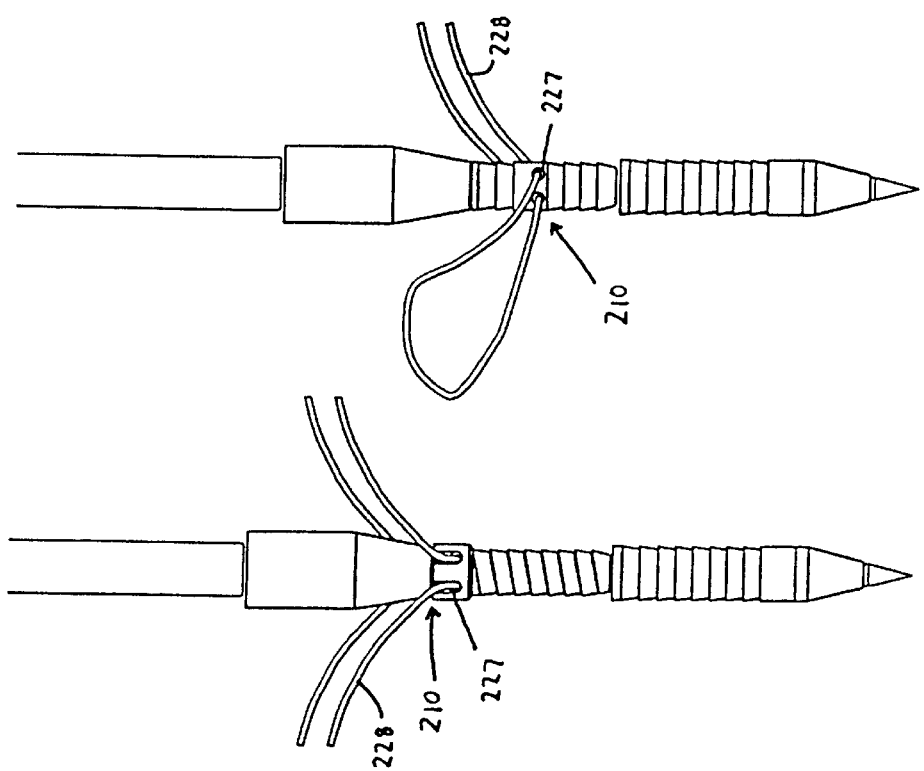

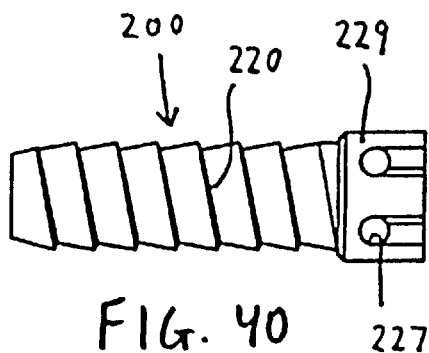
FIG. 40
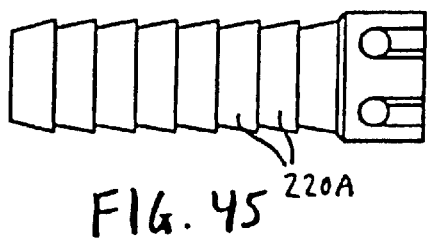 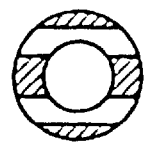 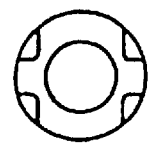
FIG. 45   FIG. 41   FIG. 42
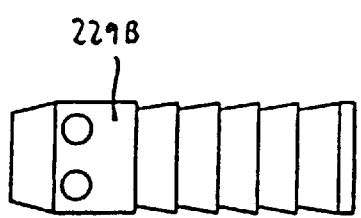 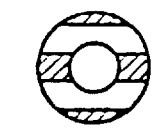 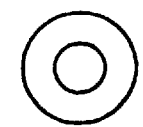
FIG. 54   FIG. 48   FIG. 49
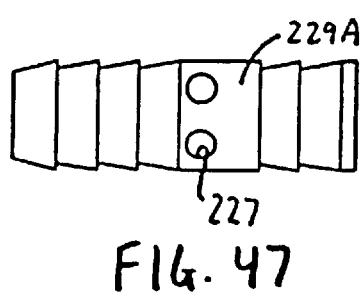
FIG. 47

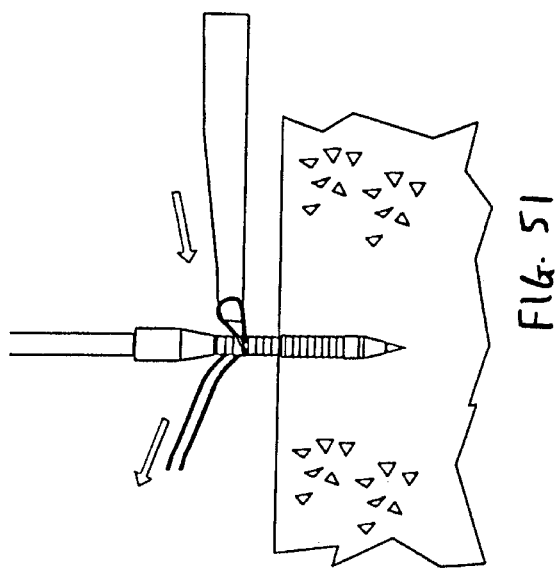
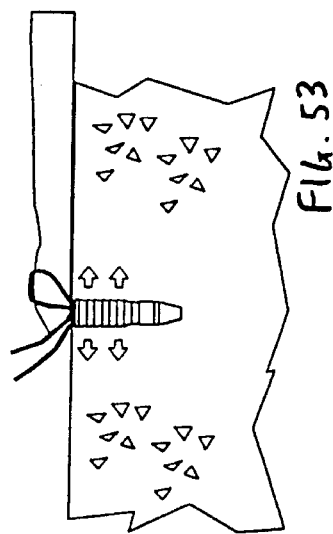
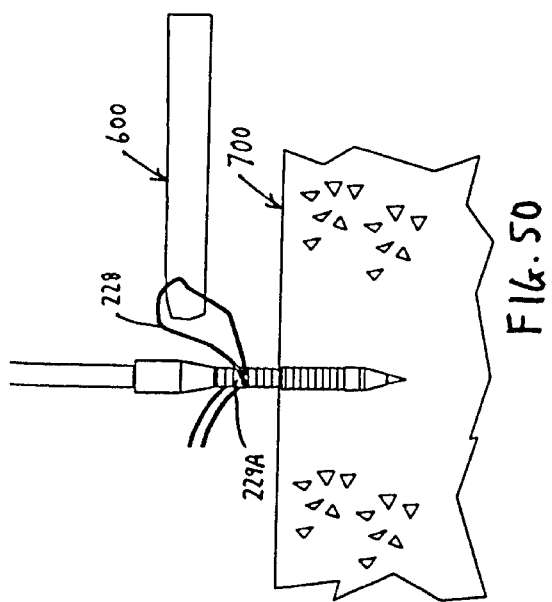
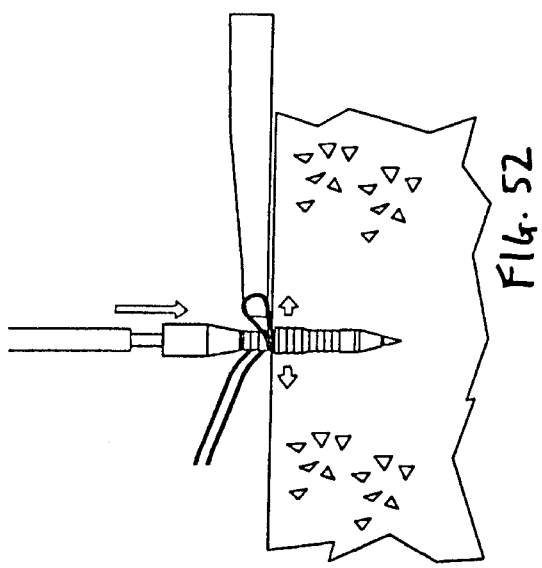

APPARATUS AND METHOD FOR ATTACHING SOFT TISSUE TO BONE

FIELD OF THE INVENTION

This invention relates generally to medical devices and procedures. More particularly, this invention relates to apparatus and methods for attaching soft tissue to bone.

BACKGROUND OF THE INVENTION

The complete or partial detachment of ligaments, tendons and/or other soft tissues from their associated bones within the body are relatively commonplace injuries, particularly among athletes. Such injuries are generally the result of excessive stresses being placed on these tissues. By way of example, tissue detachment may occur as the result of an accident such as a fall, over-exertion during a work-related activity, during the course of an athletic event, or in any one of many other situations and/or activities.

In the case of a partial detachment, the injury will frequently heal itself, if given sufficient time and if care is taken not to expose the injury to further undue stress.

In the case of complete detachment, however, surgery may be needed to re-attach the soft tissue to its associated bone or bones.

Numerous devices are currently available to re-attach soft tissue to bone. Examples of such currently-available devices include screws, staples, suture anchors and tacks.

In soft tissue re-attachment procedures utilizing screws, the detached soft tissue is typically moved back into its original position over the bone. Then the screw is screwed through the soft tissue and into the bone, with the shank and head of the screw holding the soft tissue to the bone.

Similarly, in soft tissue re-attachment procedures utilizing staples, the detached soft tissue is typically moved back into its original position over the bone. Then the staple is driven through the soft tissue and into the bone, with the legs and bridge of the staple holding the soft tissue to the bone.

In soft tissue re-attachment procedures utilizing suture anchors, an anchor-receiving hole is generally first drilled in the bone at the desired point of tissue re-attachment. Then a suture anchor is deployed in the hole using an appropriate installation tool. This effectively locks the suture to the bone, with the free end(s) of the suture extending out of the bone. Next, the soft tissue is moved into position over the hole containing the deployed suture anchor. As this is done, the free end(s) of the suture is (are) passed through or around the soft tissue, so that the free end(s) of the suture reside(s) on the far (i.e., non-bone) side of the soft tissue. Finally, the suture is used to tie the soft tissue securely to the bone.

Alternatively, in some soft tissue re-attachment procedures utilizing suture anchors of the type described above, the soft tissue may first be moved into position over the bone. Then, while the soft tissue lies in position against the bone, a single hole may be drilled through the soft tissue and into the bone. Next, a suture anchor is passed through the soft tissue and deployed in the bone using an appropriate installation tool. This results in the suture anchor being locked to the bone, with the free end(s) of the suture extending out of the bone and through the soft tissue. Finally, the suture is used to tie the soft tissue securely to the bone.

In some cases, the suture anchor may include drill means at its distal end, whereby the suture anchor can be drilled into the bone, or drilled through the soft tissue and into the bone, whereby the aforementioned drilling and anchor-deployment steps are effectively combined.

Similarly, in soft tissue re-attachment procedures utilizing tacks, the detached soft tissue is typically moved back into its original position over the bone, and then a tack-receiving hole is generally drilled through the soft tissue and into the bone. Then the tack is driven through the soft tissue and into the bone, so that the shaft and head of the tack will hold the soft tissue to the bone.

While systems and method based on the aforementioned screws, staples, suture anchors and tacks are generally effective, they also all suffer from one or more disadvantages.

OBJECTS OF THE INVENTION

Accordingly, one object of the present invention is to provide a novel apparatus and method for re-attaching soft tissue to bone which improves upon the prior art devices and techniques discussed above.

Another object of the present invention is to provide a novel apparatus and method for re-attaching soft tissue to bone which is easy to use and simple to perform.

And another object of the present invention is to provide a novel apparatus and method for re-attaching soft tissue to bone which expedites and facilitates the re-attachment procedure.

Still another object of the present invention is to provide a novel apparatus and method for re-attaching soft tissue to bone which minimizes trauma to the patient during the re-attachment procedure.

Yet another object of the present invention is to provide a novel apparatus and method for re-attaching soft tissue to bone which can be used in both open surgical procedures and in closed surgical procedures (e.g., arthroscopic or endoscopic surgical procedures) where access to the surgical site is provided by one or more cannulas.

And another object of the present invention is to provide a novel system and method for re-attaching soft tissue to bone which is also usable in the attachment of prosthetic devices, and/or grafts of natural and/or synthetic material, to bone or bone-like structures.

SUMMARY OF THE INVENTION

These and other objects of the present invention are achieved by the provision and use of a novel apparatus and method for attaching soft tissue and the like to bone.

In one preferred embodiment, the novel apparatus comprises an expandable body configured to expand into bone, the expandable body defining a bore; and an expander pin comprising a shaft sized to be received in the bore of the expandable body and expand the expandable body laterally when the expander pin is driven into the expandable body, and tissue attachment apparatus associated with the shaft, the expander pin defining a bore; whereby when the expander pin is driven into the expandable body, the expandable body will be attached to bone and the tissue attachment apparatus will secure tissue to the apparatus.

In one preferred embodiment, the novel method comprises driving an expandable fastener into a bone, the expandable fastener defining a bore and comprising tissue attachment apparatus; and fixing the expandable fastener in, and thereby securing the tissue relative to, the bone.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 5 is a side view, partially in section, of the distal end of the fastening apparatus shown in FIG. 1;

FIG. 6 is an exploded view showing the fastener, and a portion of the installation tool, of the fastening apparatus shown in FIG. 1;

FIGS. 7 and 8 are perspective, exploded views of the elements shown in FIG. 5;

FIGS. 9–11 show details of the distal tip member of the fastener shown in FIG. 5;

FIGS. 12 and 13 show details of the proximal main member of the fastener shown in FIG. 5;

FIG. 31 is a side view showing an alternative form of proximal main member for a fastener formed in accordance with the present invention;

FIG. 32 is a side view showing an alternative form of distal tip member for a fastener formed in accordance with the present invention;

FIGS. 39–42 show details of the construction of an alternative form of fastener also formed in accordance with the present invention;

FIG. 45 shows details of an alternative form of expander pin for the fastener shown in FIGS. 39–44;

FIGS. 46–49 show details of the construction of another alternative form of fastener also formed in accordance with the present invention;

FIGS. 50–53 show the fastener of FIGS. 46–49 being used to attach soft tissue (or the like) to bone;

FIG. 54 shows details of an alternative form of expander pin for the fastener shown in FIGS. 46–53;

DETAILED DESCRIPTION OF THE PREFERRED EMBODIMENT

Figure 1:
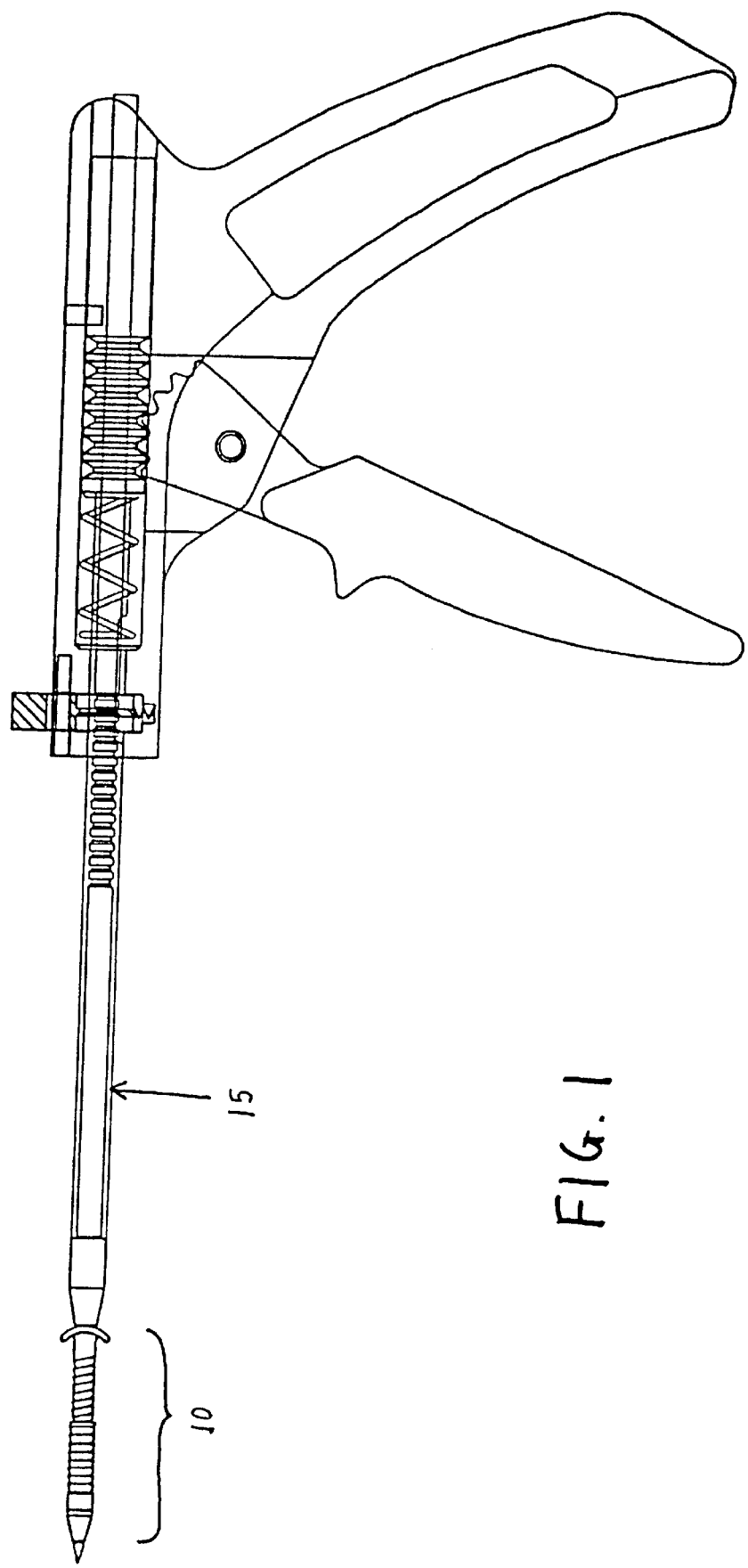
FIG. 1 is a side view of a novel fastening apparatus formed in accordance with the present invention.
Figure 2:
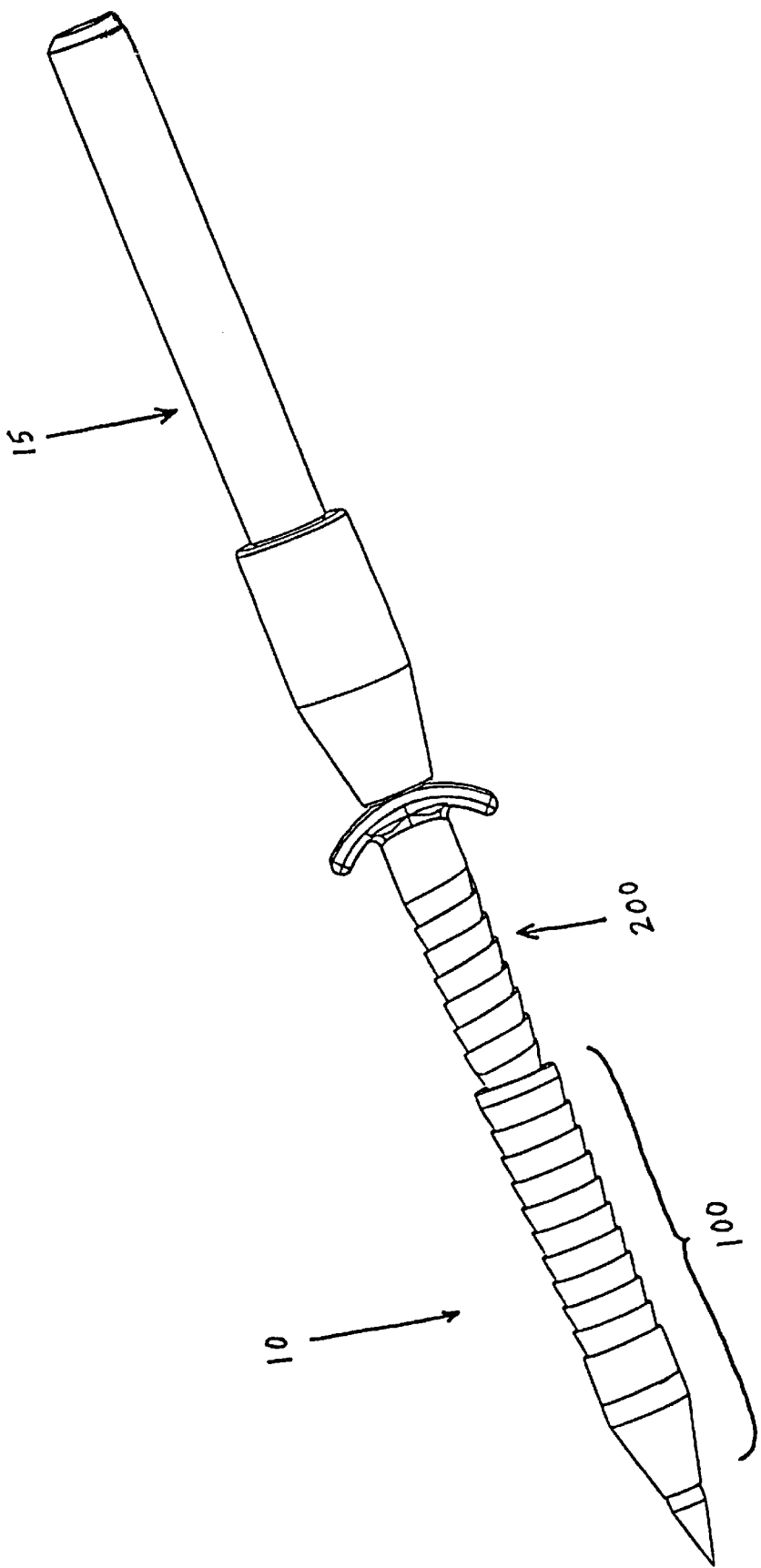
FIGS. 2–4 are perspective views of the distal end of the fastening apparatus shown in FIG. 1.
Figure 3:
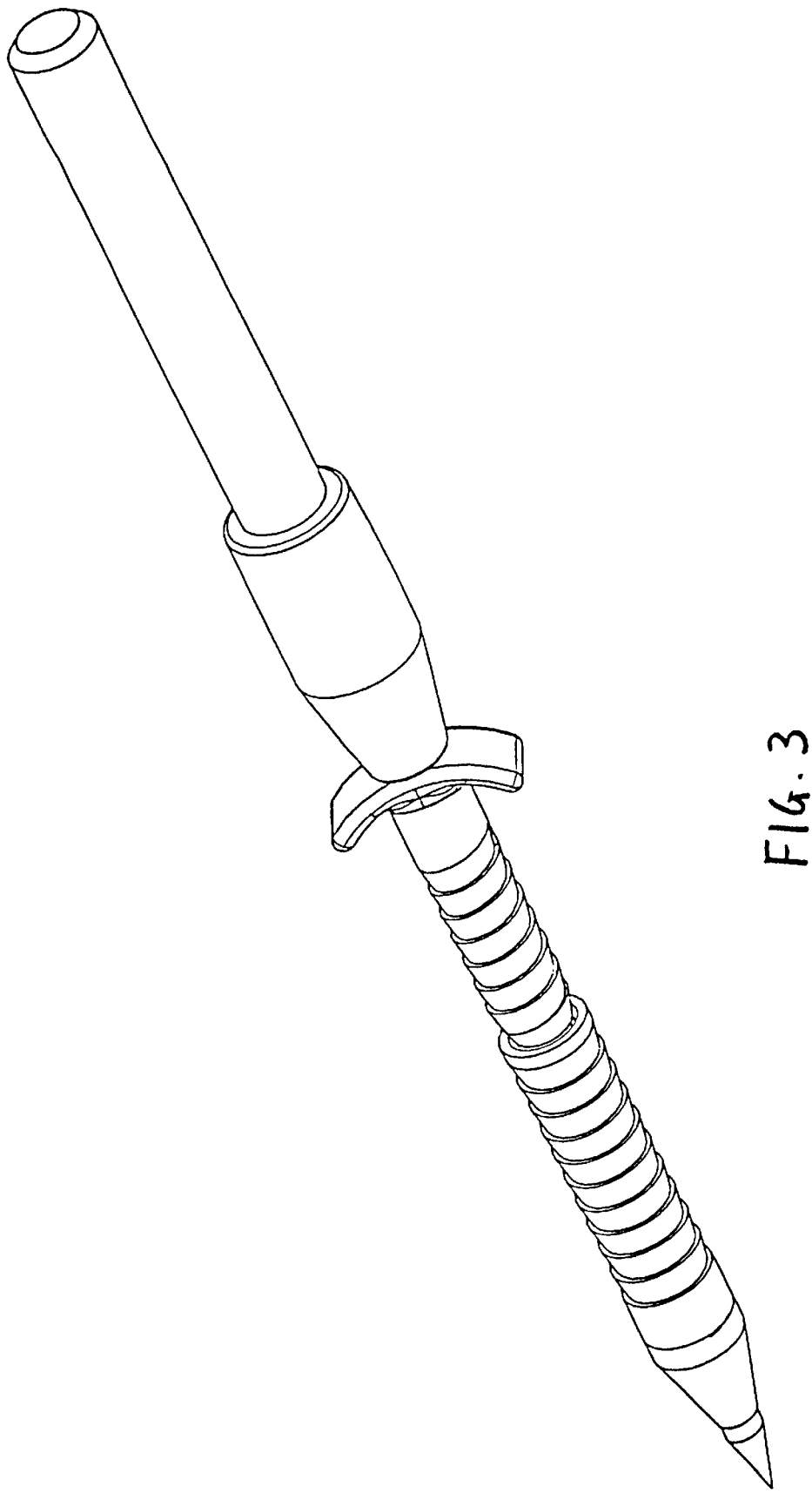
Figure 4:
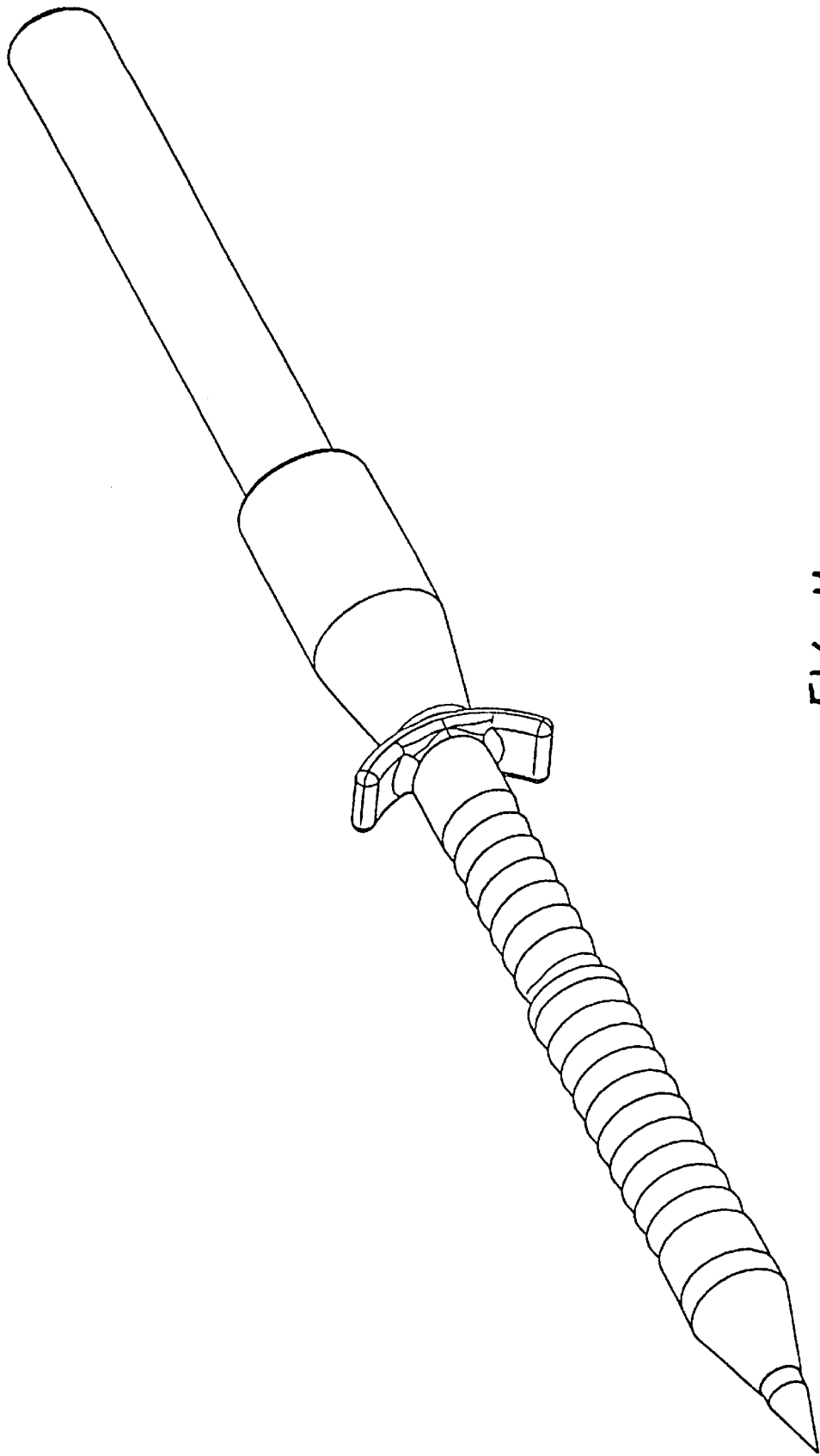
Figure 7:
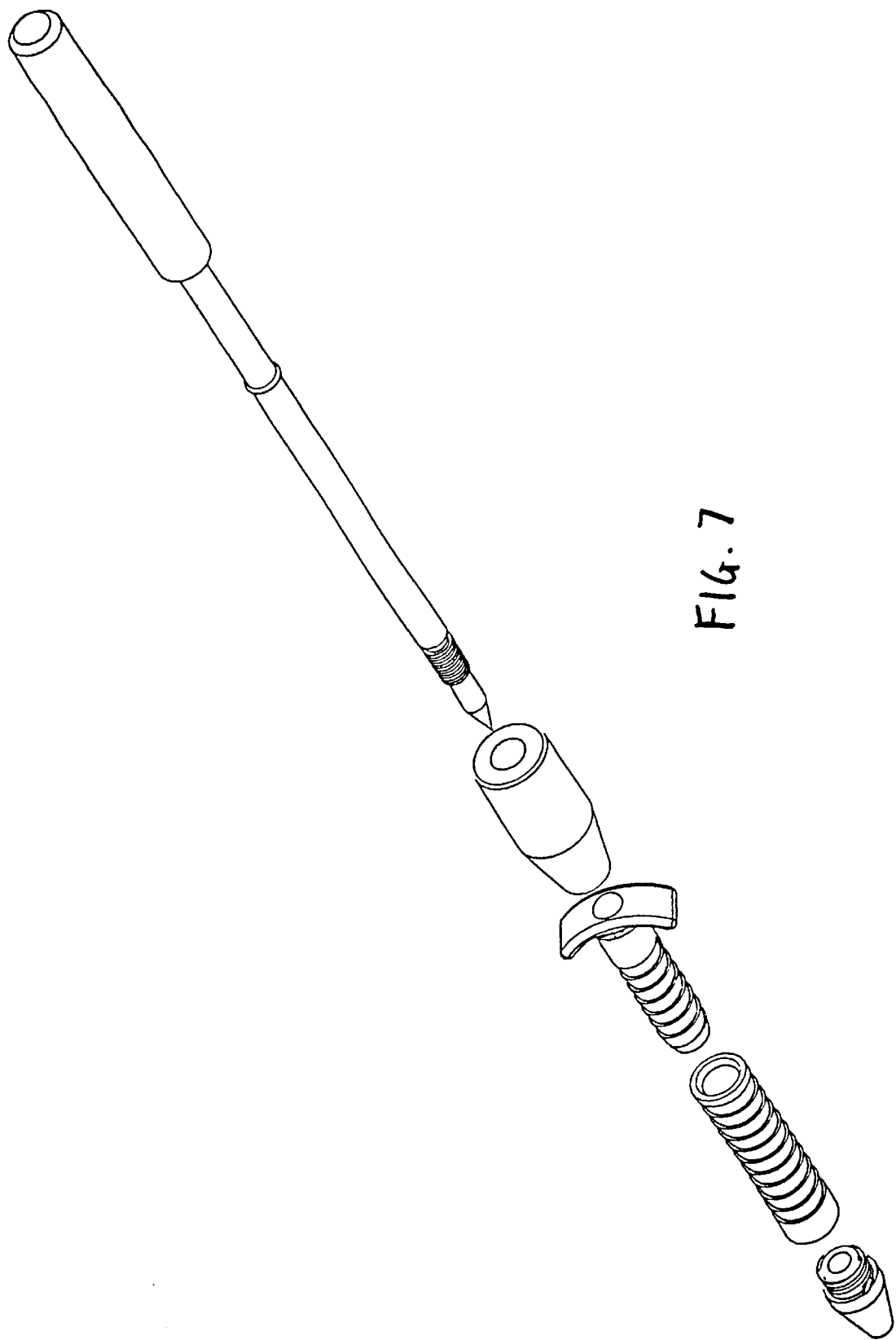
Figure 15:
FIGS. 14–16 show details of the expander pin of the fastener shown in FIG. 5.

Looking first at FIG. 1, there is shown a fastening apparatus 5 for attaching soft tissue (or the like) to bone. Fastening apparatus 5 generally comprises a fastener 10 and an installation tool 15.

Looking next at FIGS. 1–8, fastener 10 generally comprises an expandable body 100 (FIG. 2) and an expander pin 200.

Expandable body 100 comprises a generally frusto-conical distal end 105 (FIG. 5) characterized by a frusto-conical outer surface 110 terminating in a distal end surface (or rim) 115, and a generally cylindrical proximal end 120 terminating in a proximal end surface 125. A central passageway 130 extends through expandable body 100, from distal end surface 115 to proximal end surface 125.

In a preferred form of the invention, central passageway 130 comprises a bore 135 opening on distal end surface 115, a threaded section 140, and a bore 145 opening on proximal end surface 125.

Expandable body 100 preferably also comprises bone securement apparatus 150 formed on proximal end 120 for facilitating securement of fastener 10 to bone, as will hereinafter be discussed in further detail. In one preferred form of the invention, bone securement apparatus 150 comprises a plurality of frusto-conical ribs 155. Ribs 155 are tapered, distally-to-proximally, so as to (1) facilitate insertion of expandable body 100 into bone in a distal direction, and (2) resist withdrawal of expandable body 100 from bone in a proximal direction.

If desired, expandable body 100 can be formed out of a single piece of material. Preferably, however, and looking now at FIGS. 1–13, expandable body 100 comprises a distal tip member 160 (FIG. 9) and a proximal main member 165 (FIG. 12).

Distal tip member 160 (FIGS. 9–11) preferably comprises the aforementioned frusto-conical outer surface 110, distal end surface (or rim) 115, internal bore 135, and threaded section 140. Distal tip member 160 also preferably comprises a proximally-extending, threaded projection 170. Proximally-extending threaded projection 170 serves to secure distal tip member 160 to proximal main member 165, as will hereinafter be discussed in further detail.

Proximal main member 165 (FIGS. 12 and 13) preferably comprises the aforementioned proximal end surface 125, bore 145 and bone securement apparatus 150 (preferably in the form of frusto-conical ribs 155). Proximal main member 165 also comprises a threaded counterbore 175 at its distal end. Threaded counterbore 175 is sized and shaped so as to matingly receive proximally-extending threaded projection 170 of distal tip member 160, whereby the two elements may be secured to one another so as to form the complete expandable body 100.

Figure 57:
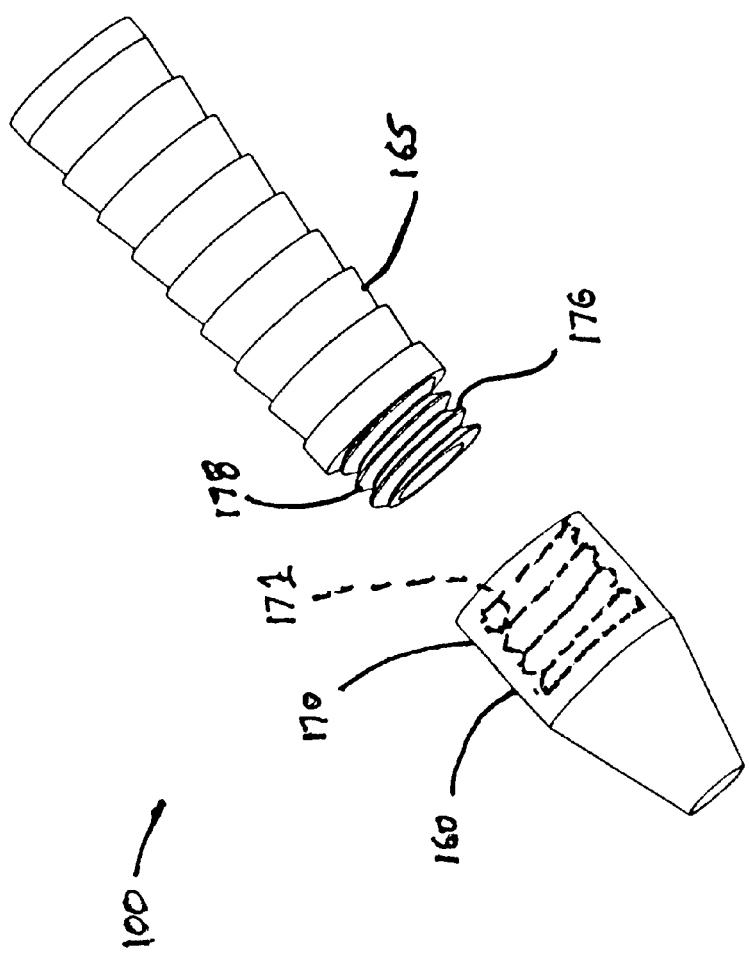
FIG. 57 illustrates an alternative embodiment of expandable body.

Referring to FIG. 57, it will be seen that in an alternative embodiment proximally-extending threaded projection 170 of the distal tip member 160 is of an annular configuration and is provided with internal threads 172. Proximal main member 165 includes a projection 176 having external threads 178 thereon for engagement with the distal tip member internal threads 172. Threaded projection 170 is sized and shaped so as to matingly receive threaded projection 176 of main member 165, whereby the two elements 160, 165 may be secured to one another so as to form the complete expandable body 100.

A primary advantage of forming expandable body 100 out of two separate components (i.e., distal tip member 160 and proximal main member 165) is that each component can be optimized for its own function. More particularly, inasmuch as distal tip member 160 is intended to help open a passageway in bone to receive the overall fastener 10, distal tip member 160 is preferably formed out of a relatively hard material. At the same time, however, inasmuch as proximal main member 165 is intended to expand radially outwardly during deployment of the fastener so as to fix expandable body 100 (and hence the complete fastener 10) to bone, proximal main member 165 is preferably formed out of a relatively soft and easily expandable material.

Fastener 10 also comprises the expander pin 200. Looking next at FIGS. 1–8 and 14–16, expander pin 200 generally comprises a shaft 205 and tissue attachment apparatus 210 associated with shaft 205. Shaft 205 is sized so that it will not normally fit within central passageway 130 (FIG. 5) of expandable body 100. However, shaft 205 is also sized so that when expander pin 200 is driven longitudinally into expandable body 100, the expander pin will force the side walls of expandable body 100 to expand radially outwardly against adjacent bone, whereby the expandable body (and hence the entire fastener) will be secured to a host bone, as will hereinafter be discussed in further detail.

Preferably, shaft 205 includes fastener stabilization apparatus 215 for stabilizing the longitudinal position of expander pin 200 relative to expandable body 100, as will hereinafter be discussed in further detail. More particularly, fastener stabilization apparatus 215 is adapted to resist withdrawal of expander pin 200 from expandable body 100 once expander pin 200 has been driven into expandable body 100, as will hereinafter be discussed in further detail. In one preferred form of the invention, fastener stabilization apparatus 215 comprises a screw thread 220 formed on the outer surface of shaft 205.

Figure 14:
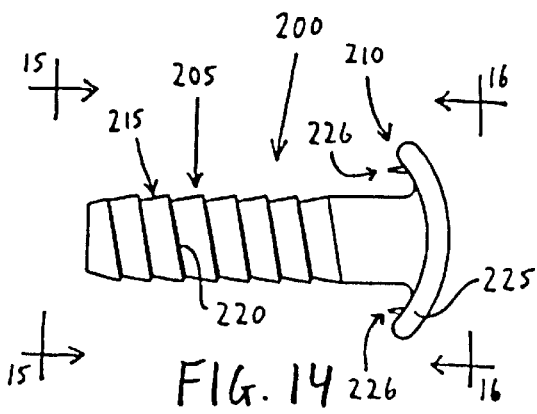
Figure 16:
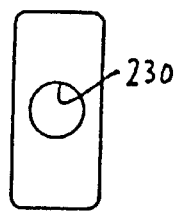
Figure 58:
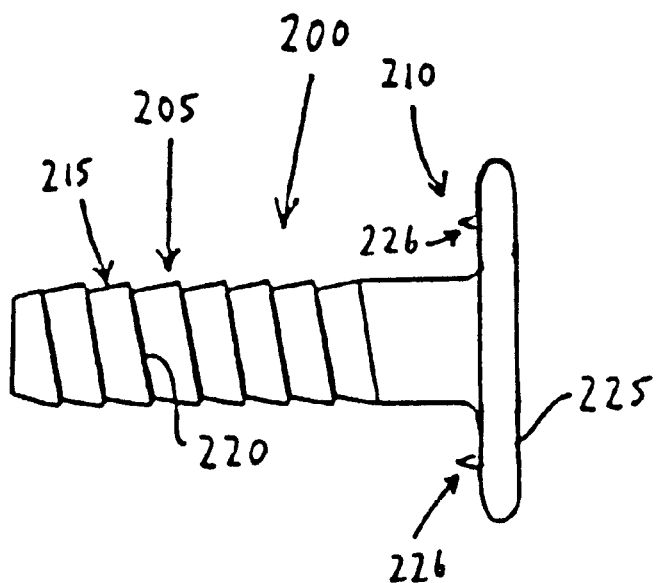
FIG. 58 illustrates an alternative embodiment of the expander pin.
Figure 59:
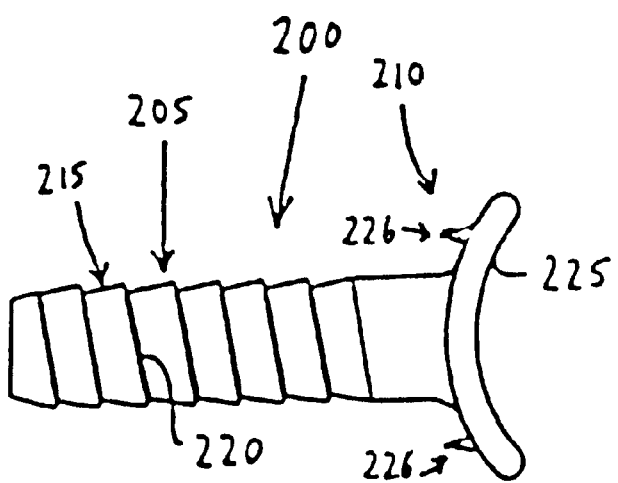
FIG. 59 illustrates another alternative embodiment of the expander pin.

Still looking now at FIGS. 1–8 and 14–16, in one preferred form of the invention, tissue attachment apparatus 210 comprises one or more lateral projections 225 adjacent to the proximal end of the shaft. The one or more lateral projections 225 collectively form a fastener head for holding tissue to bone, as will hereinafter be discussed in further detail. Lateral projections 225 may be formed with a substantially convex configuration, as shown in FIG. 14; or lateral projections 225 may be formed with a substantially planar configuration, as shown in FIG. 58; or lateral projections 225 may be formed with a substantially concave configuration as shown in FIG. 59. Furthermore, if desired, one or more distally-projecting longitudinal projections 226 (FIG. 14) may be formed on the distal side of lateral projections 225 for enhancing the engagement of lateral projections 225 with underlying tissue.

Expander pin 200 includes a longitudinal passageway 230 extending the length of the expander pin.

Fastener 10 is intended to be used in conjunction with installation tool 15. Looking next at FIGS. 1–8, installation tool 15 comprises a shaft 300 (FIG. 6) terminating in a tapered distal point 310. Tapered distal point 310 is preferably formed so as to be relatively hard, whereby it can open a passageway in bone to receive the overall fastener 10, as will hereinafter be discussed in further detail. Threads 315 are formed on shaft 300 proximal to tapered distal point 310.

Shaft 300 is sized so that it may be received in the central passageway 130 (FIG. 5) of expandable body 100, and in longitudinal passageway 230 (FIG. 16) of expander pin 200. Threads 315 of shaft 300 are sized and positioned so that when fastener 10 (i.e., expandable body 100 and expander pin 200)-is mounted on shaft 300, shaft threads 315 can mate with the expandable body's threads 140, whereby expandable body 100 can be secured to the distal end of shaft 300. In one preferred form of the invention, the shaft's tapered distal point 310 and the expandable body's frusto-conical outer surface 110 (FIG. 9) are coordinated with one another so that when expandable body 100 is screwed onto shaft 300, the expandable body's frusto-conical outer surface 110 will form, in a rough sense, a continuation, or extension, of the taper of the shaft's tapered distal point 310 (FIG. 5).

Preferably, the installation tool's shaft 300 comprises a thinner distal section 320 (FIG. 5) proximal to the shaft's tapered distal point 310 and distal to the shaft's threads 315, and a trailing section 325 proximal to shaft threads 315, and a thicker proximal section 330 proximal to trailing section 325. Trailing section 325 and thicker proximal section 330 together define an annular shoulder 335 at their intersection. A rib 340 is preferably formed on trailing section 325, distal to annular shoulder 335.

A pusher 400 (FIGS. 5 and 17) is preferably mounted on shaft 300. Pusher 400 is used to help deploy fastener 10 in bone, by transferring a force applied to the proximal end of pusher 400 onto a fastener 10 located at the distal end of pusher 400. In the process, pusher 400 acts as a sort of safeguard to prevent the proximal end of fastener 10 (i.e., the proximal end of expander pin 200) from being damaged during the application of such force. Pusher 400 preferably comprises a tapered distal portion 405 characterized by a tapered outer surface 410 terminating in a distal end surface 415, and a cylindrical proximal portion 420 characterized by a cylindrical outer surface 425 terminating in a proximal end surface 427. Pusher 400 has a central bore 430 extending therethrough. Bore 430 is sized so that it will form a close sliding fit with rib 340 (FIG. 6) of shaft 300. A lip 435 (FIG. 17) protrudes into central bore 430 adjacent to the pusher's proximal end surface 427. Lip 435 is sized so that it may not pass by rib 340 of shaft 300.

Figure 20:
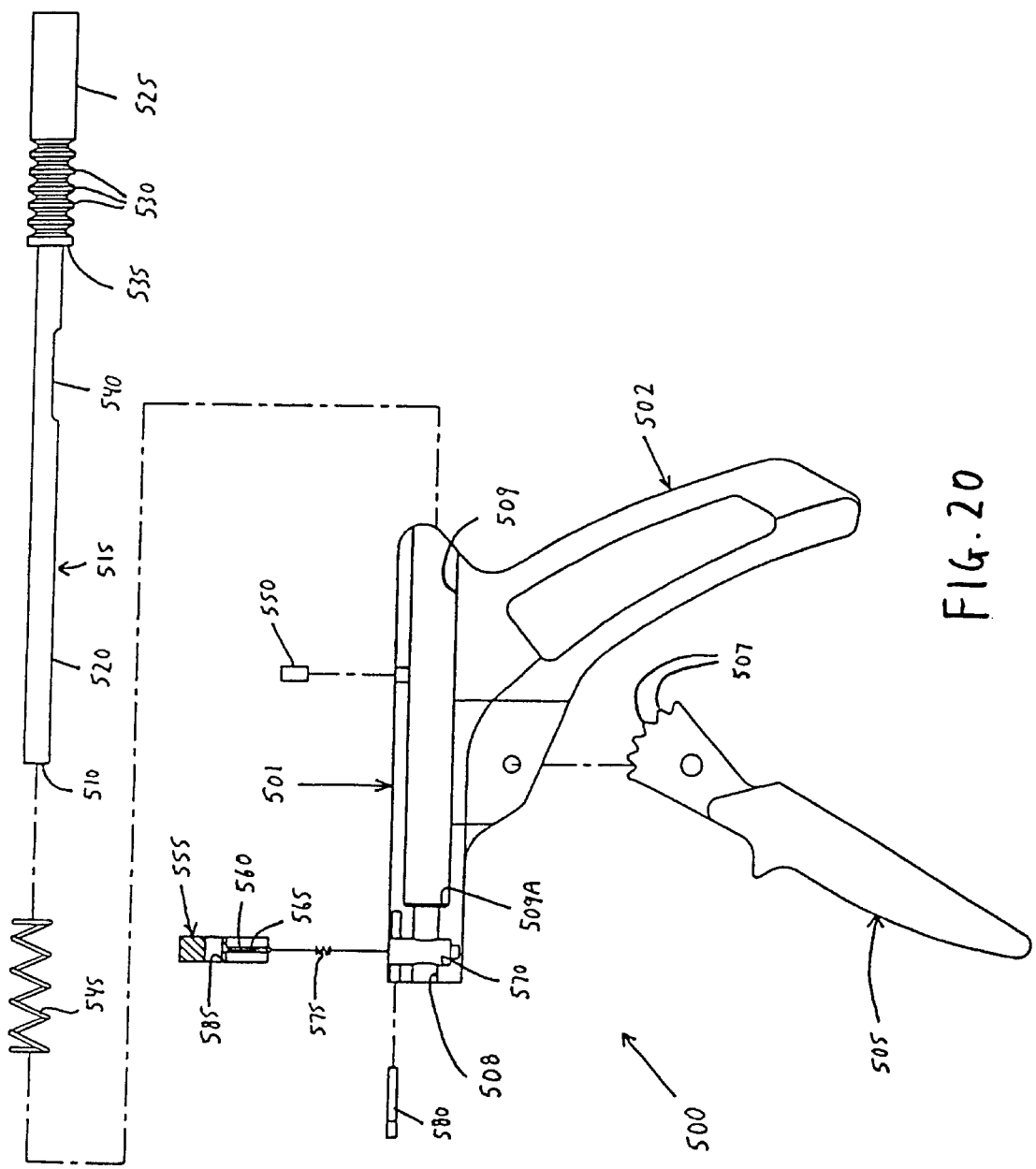
FIG. 20 is an exploded side view of the handle assembly of the installation tool shown in FIG. 1.

In one preferred form of the invention, shaft 300 includes a plurality of ribs 345 (FIG. 6) on the shaft's thicker proximal section 330, and installation tool 15 includes a handle assembly 500 (FIG. 20). Each rib 345 includes an inclined surface 345A disposed on the proximal side of the rib (FIG. 6). The distal side of each rib 345 extends substantially perpendicular to the longitudinal axis of shaft 300.

Handle assembly 500 comprises a body 501 having a handle grip 502. A trigger 505, having a plurality of fingers 507, is pivotally connected to body 501. Body 501 also comprises a bore 508 opening on the body's distal end, and a counterbore 509 opening on the body's proximal end. A shoulder 509A is formed at the intersection of bore 508 and counterbore 509.

Handle assembly 500 also comprises a hollow ram 515. Ram 515 is sized so that it can slidably accommodate shaft 300, as will hereinafter be discussed in further detail. Ram 515 comprises a narrower distal portion 520 terminating in a distal tip 510, and a wider proximal portion 525 including a plurality of teeth 530. A shoulder 535 is formed at the intersection of narrower distal portion 520 and wider proximal portion 525. A slot 540 extends through the side wall of narrower distal portion 520.

Ram 515 is mounted in body 510 in the manner shown in FIGS. 1 and 20, i.e., so that (1) the ram's narrower distal portion 520 extends through, and protrudes from, the body's bore 508, (2) the ram's wider proximal portion 525 is disposed in the body's counterbore 509, and (3) the trigger's fingers 507 engage the ram's teeth 530. As a result of this construction, moving trigger 505 will cause ram 515 to move relative to body 501. A spring 545 is positioned in body 501, between body shoulder 509A and ram shoulder 535, so as to bias ram 515 in a proximal direction. A stop pin 550 extends into counterbore 509 so as to limit proximal movement of ram 515.

Handle assembly 500 also comprises a gate 555 which includes an opening 560 therein. Opening 560 defines a bottom wall 565 thereof. Gate 555 is disposed in an opening 570 formed in body 501. A spring 575 biases gate 555 against a locking pin 580, which extends through an oversized hole 585 formed in gate 555. Gate 555 is disposed in body 501 so that the gate's bottom wall 565 normally protrudes, via ram slot 540, into the interior of ram 515; however, pressing gate 555 downward against the power of spring 575 will permit the gate's bottom wall 565 to be removed from the interior of ram 515.

In use, and as will hereinafter be discussed in further detail, handle assembly 500 is loaded over the proximal end of shaft 300, and moved proximally down the shaft until the gate's bottom wall 565 starts to engage the ribs 345 of shaft 300. As this occurs, the inclined proximal surfaces 345A of ribs 345 will allow the handle assembly 500 to be moved distally along shaft 300 to the extent desired. However, since inclined surfaces 345A are provided on only the proximal sides of ribs 345, the geometry of the ribs will prevent handle assembly 500 from moving back proximally along the shaft, unless gate 555 is pressed downward against the power of spring 575 so as to move the gate's bottom wall 565 out of engagement with the shaft's ribs. Handle assembly 500 is moved down shaft 300 until the ram's distal end surface 510 engages, or substantially engages, the proximal end 427 of pusher 400. Thereafter, pulling of the handle assembly's trigger 505 will cause ram 515 to move distally along shaft 300, whereby pusher 400 can drive expander pin 200 into expandable body 100 so as to set the expandable body in bone, as will hereinafter be discussed in further detail.

The use of handle assembly 500 in conjunction with shaft 300 is often preferred, since it permits shaft 300 to be held in place while ram 515 is advanced down shaft 300. More particularly, inasmuch as handle assembly 500 is releasably secured to shaft 300 via the engagement of handle gate 555 with shaft ribs 345, handle assembly 500 can stabilize shaft 300 even as the handle's ram 515 is advancing down shaft 300. This has been found to be advantageous in many circumstances. However, it should also be appreciated that fastener 10 can be set without using handle assembly 500, as will hereinafter also be discussed in further detail.

Looking next at FIGS. 21–25, there is shown a general method for attaching soft tissue (or the like) to bone using the fastener of the present invention. In particular, the invention will be discussed in the context of (1) a fastener 10 comprising an expandable body 100 and an expander pin 200; (2) an installation tool 15 comprising a shaft 300; and (3) a pusher 400 mounted on shaft 300.

Figure 17:
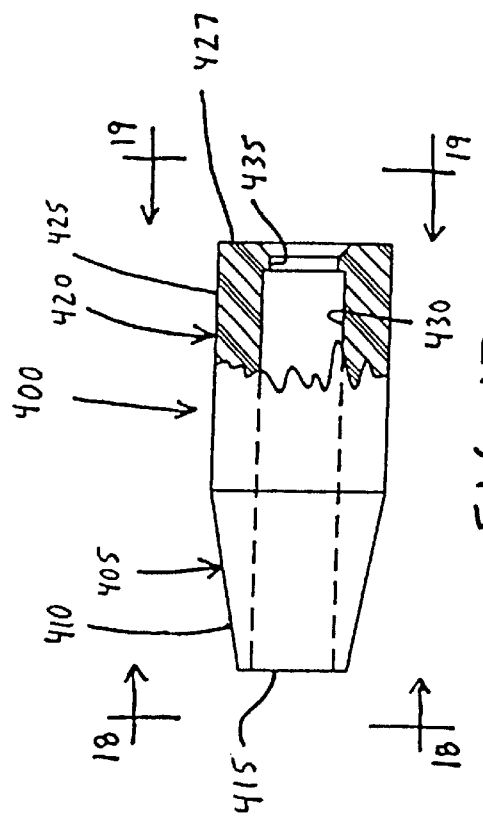
Figure 18:
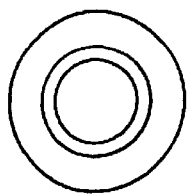

The foregoing fastening system is prepared for use by first passing pusher 400 proximally over the distal end of shaft 300 until the pusher's proximal end surface 427 (FIG. 17) engages, or approximately engages, the shaft's annular shoulder 335 (FIG. 6). Then the fastener's expander pin 200 is passed proximally over the distal end of shaft 300 until the proximal end of expander pin 200 engages, or approximately engages, the pusher's distal end surface 415 (FIG. 17). Next, the fastener's expandable body 100 is passed proximally over the distal end of shaft 300 until the proximal end of the expandable body's threaded section 140 (FIG. 5) engages the distal end of the shaft's threads 315 (FIG. 6). Then the fastener's expandable body 100 is screwed onto shaft 300. At this point, the proximal end surface 125 (FIG. 12) of expandable body 100 will engage, or approximately engage, the distal end surface of expander pin 200. It will be appreciated that at this point, the expandable body 100, expander pin 200 and pusher 400 will be held relatively immobile on shaft 300, by virtue of shaft shoulder 335 (FIG. 6) and shaft threads 315 and the sizing of the elements held therebetween.

Figure 21:
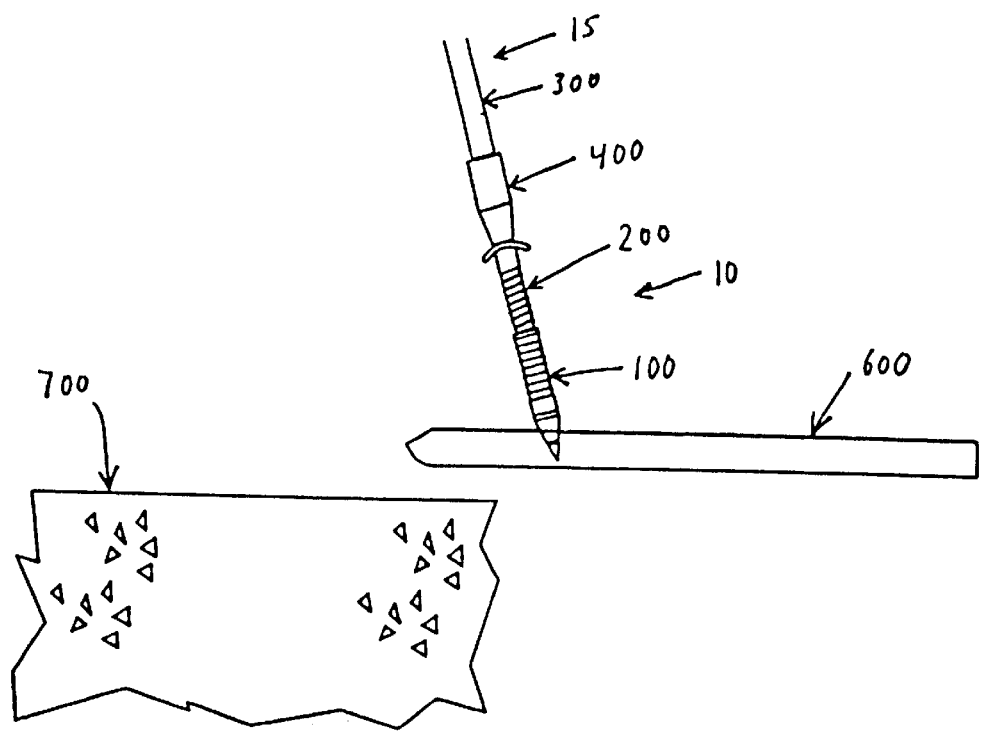
FIGS. 21–25 show the novel fastening apparatus of the present invention being used to attach soft tissue (or the like) to bone.
Figure 22:
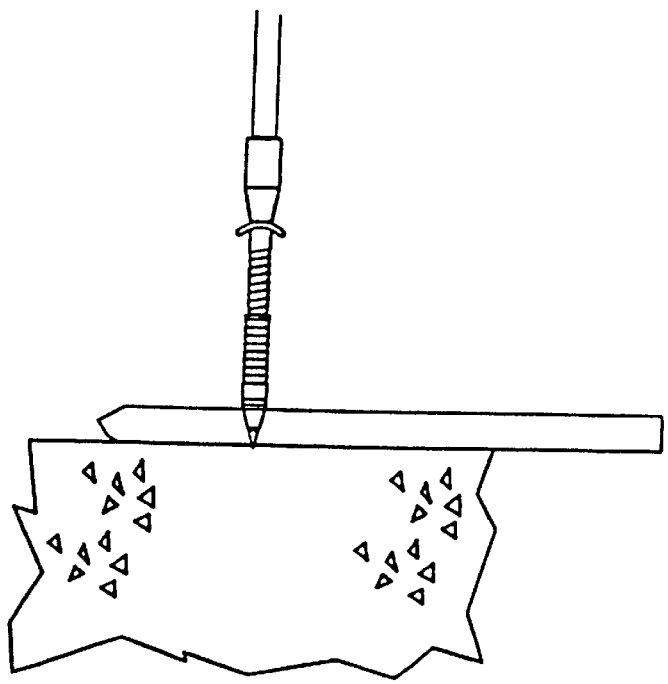

Next, soft tissue (or the like) 600 is "stabbed" with the sharp distal point of shaft 300 and dragged to its desired position against bone 700 (FIG. 21). Alternatively, soft tissue 600 may be gripped by another instrument (e.g., forceps or the like) and moved into position against bone 700.

Figure 23:
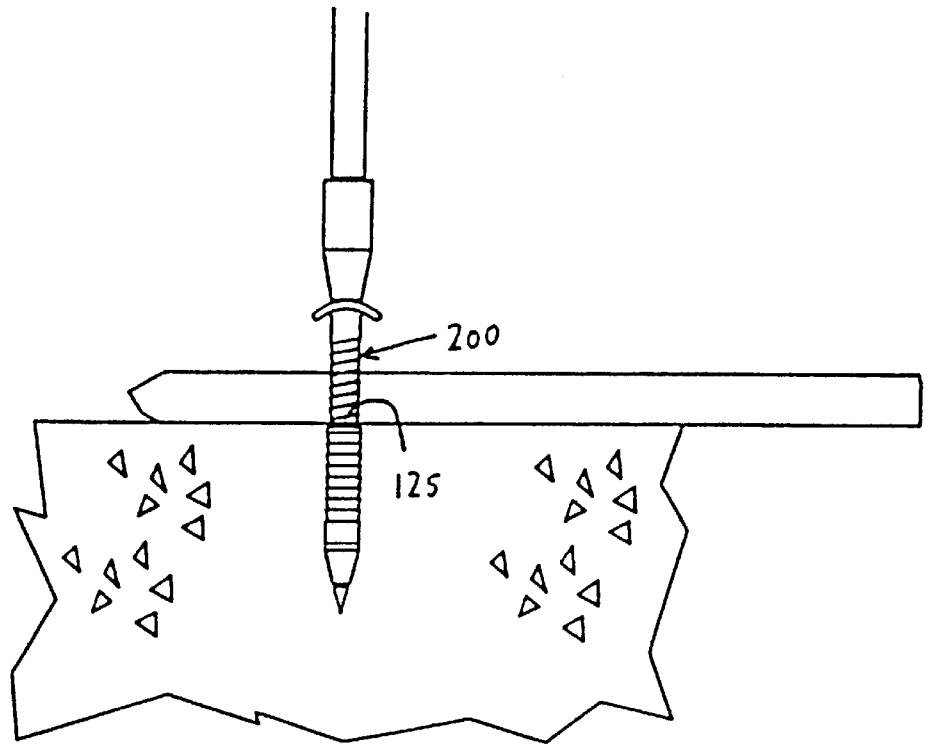

Then, with soft tissue 600 in position against bone 700, shaft 300 is forced distally through tissue 600 (FIG. 22) and into bone 700 (FIG. 23). It will be appreciated that, as this occurs, expandable body 100 will be carried into the bone, due to the screw engagement established between expandable body 100 and shaft 300. In fact, the tapered distal ends of shaft 300 and expandable body 100 will cooperate with one another so as to force an opening in the soft tissue and the bone, without any need for pre-drilling. Shaft 300 is preferably driven into bone 700 until the proximal end surface 125 of expandable body 100 is approximately even with the outer surface of bone 700 (FIG. 23). If desired, markings (not shown) may be placed on the outer surface of the fastener's expander pin 200 so that, once the thickness of soft tissue 600 is known, proper depth penetration can be achieved.

Figure 24:
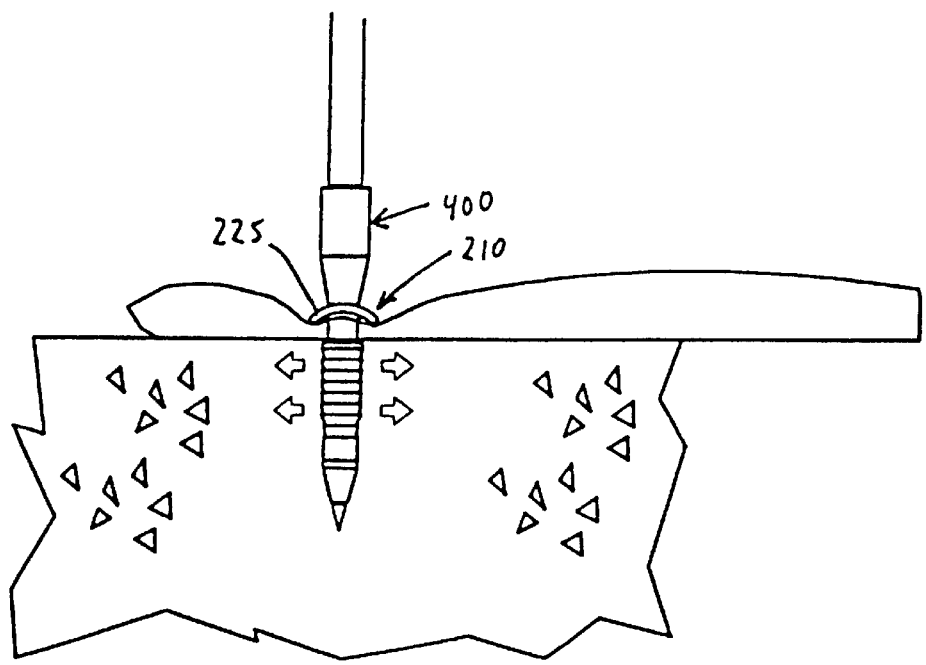
Figure 25:
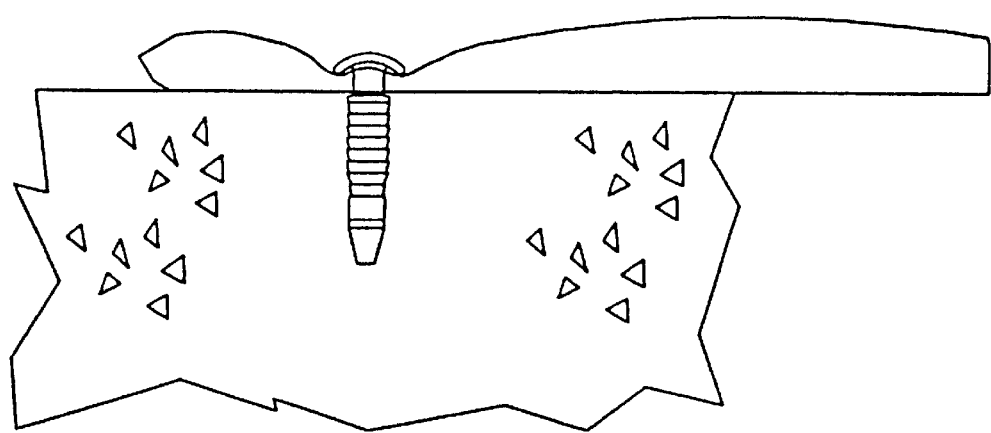

Next, the proximal end of pusher 400 is engaged with another element (not shown in FIGS. 21–25, but shown in subsequent figures) so as to move the pusher distally along shaft 300. Pusher 400 is moved distally so as to drive expander pin 200 distally, into the central passageway 130 (FIG. 5) of expandable body 100, whereby to drive the side walls of expandable body 100 radially outwardly into bone 700 and thereby secure fastener 10 to bone 700 (FIG. 24). At the same time, the fastener's tissue attachment apparatus 210 will secure soft tissue 600 to the bone. More particularly, as seen in FIG. 24, the head of expander pin 200 (made up of one or more lateral projections 225) will bear distally against soft tissue 600, whereby to keep the soft tissue fixed against bone 700.

Finally, shaft 300 is unscrewed from the expandable body's threads 140 (FIG. 5) and removed (FIG. 25), leaving fastener 10 securing soft tissue 600 to bone 700.

In the embodiment shown in FIG. 57, widthwise expansion of the proximal main member 165 serves to urge the external threads 178 of the projection 176 into firm engagement with the internal threads 172 of the distal tip member 160. Thus, the distal tip member 160 is securely held in place by the expanded proximal main member 165 to permit the shaft 300 to be unscrewed from the expandable body threads 140 and removed.

Figure 26:
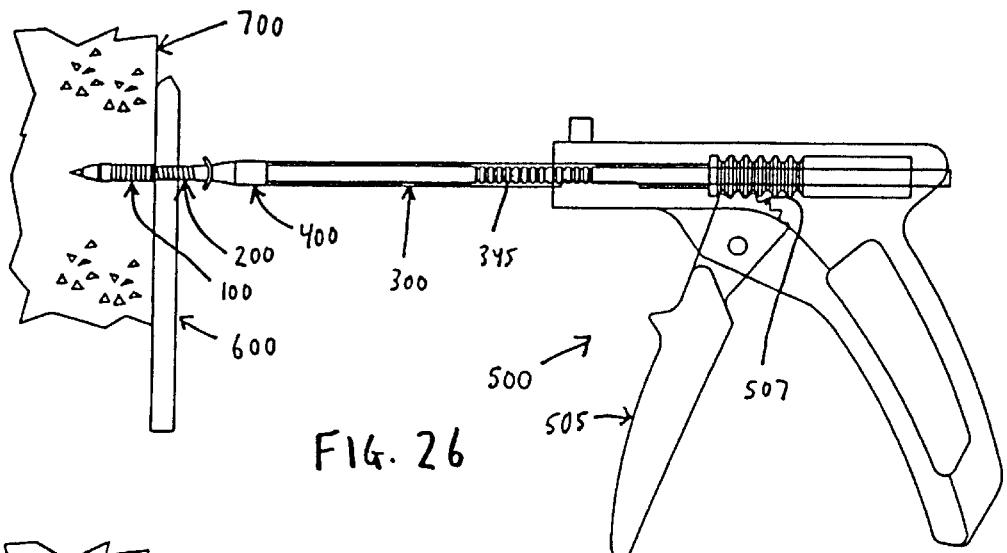
FIGS. 26–28 illustrate one preferred form of the novel fastening apparatus of the present invention being used to attach soft tissue (or the like) to bone.
Figure 27:
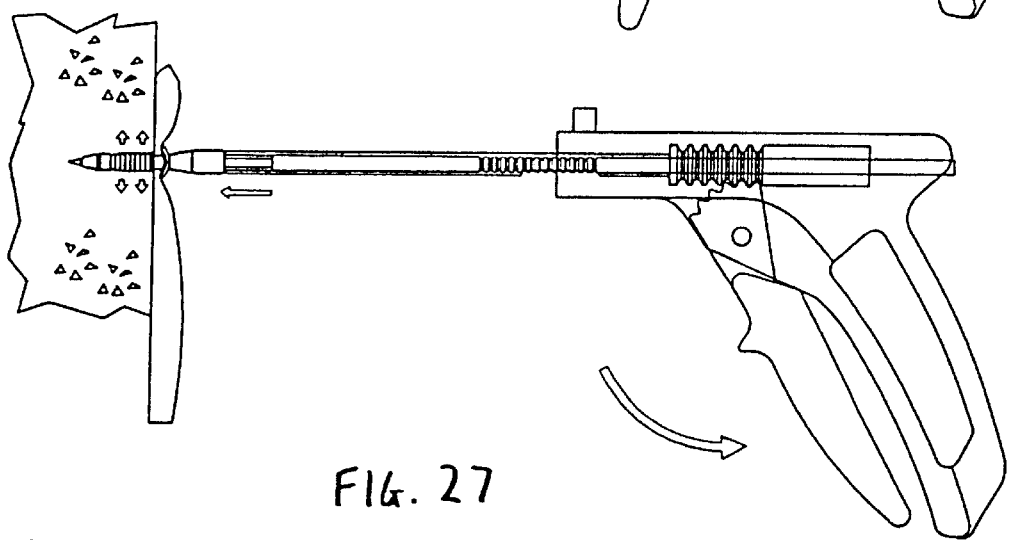
Figure 28:
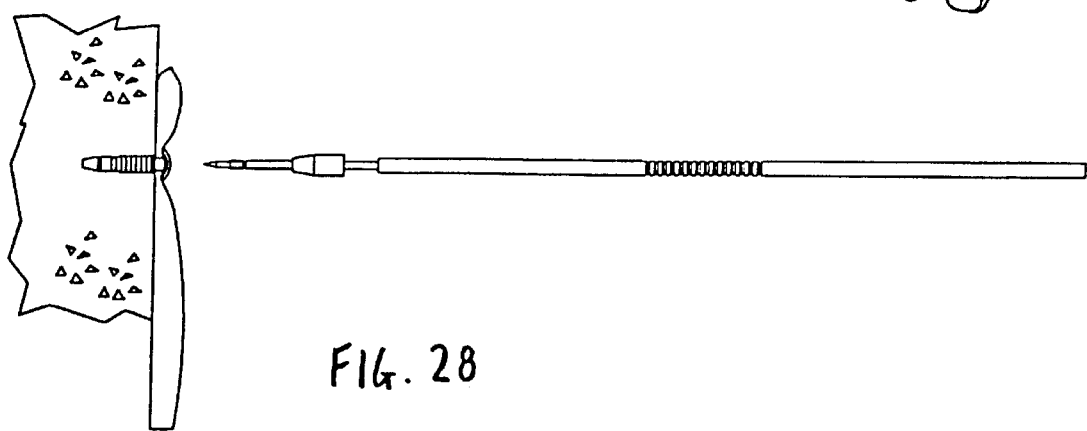

As noted above, in one preferred form of the invention, installation tool 15 is constructed so that shaft 300 includes ribs 345 (FIG. 6) adjacent its proximal end, and the installation tool includes handle assembly 500 (FIG. 20). FIGS. 26–28 illustrate how soft tissue 600 may be attached to bone 700 using such an arrangement. More particularly, after pusher 400, expander pin 200 and expandable body 100 have been attached to shaft 300 in the manner described above with respect to FIGS. 21–25, and either before or after shaft 300 is driven through soft tissue 600 and into bone 700 to the point shown in FIGS. 23 and 26, handle assembly 500 is passed distally over the proximal end of shaft 300 until the gate 555 engages ribs 345 of shaft 300. Handle assembly 500 is then pushed further down shaft 300 until the distal tip 510 of ram 515 engages the proximal end of pusher 400. Then trigger 505 is activated so as to move ram 515 distally relative to pusher 400 and fastener 10, whereby the distal tip 510 (FIG. 20) of the handle assembly's ram 515 will drive distally against the proximal end of pusher 400. This will cause pusher 400 to move expander pin 200 distally, whereby to fix fastener 10 in bone 700, with the fastener's head fixing soft tissue 600 to bone 700 (FIG. 27). Then handle assembly 500 is removed proximally off shaft 300, i.e., by first pressing gate 555 downward against the power of spring 575 so as to move the gate's bottom wall 565 out of engagement with ribs 345, and then pulling the handle assembly 500 proximally off the shaft. Then shaft 300 is unscrewed from the expandable body's threads 140 and removed from the surgical site (FIG. 28).

It will be appreciated that, by virtue of the relative sizing of shaft rib 340 (FIG. 6) and pusher lip 435 (FIG. 17), pusher 400 will be slidably retained on the distal end of shaft 300 even after shaft 300 has been unscrewed from fastener 10, since pusher lip 435 will be unable to move past shaft rib 340.

As noted above, the use of handle assembly 500 in conjunction with shaft 300 is frequently preferred, since it permits shaft 300 to be held in place while ram 515 is advanced down shaft 300. More particularly, inasmuch as handle assembly 500 is releasably secured to shaft 300 via the engagement of handle gate 555 with shaft ribs 345, handle assembly 500 can stabilize shaft 300 even as the handle's ram 515 is advancing down shaft 300. In other words, since the fastener's expandable body 100 is connected to shaft 300 by the expandable body's threaded section 140 and shaft threads 315, and inasmuch as handle assembly 500 is releasably secured to shaft 300 via the engagement of handle gate 555 with shaft ribs 345, the handle assembly can advance its ram 515 against the fastener's expander pin 200 even while the handle assembly is holding the shaft 300, and hence the fastener's expandable body 100, in place. In effect, the use of handle assembly 500 in conjunction with shaft 300 permits a proximally-directed counterforce to be applied to expandable body 100 even as a distally-directed setting force is being applied to expander pin 200.

However, it should also be appreciated that fastener 10 can be set without using handle assembly 500, as will hereinafter be discussed in further detail.

Thus, in another preferred form of the invention, installation tool 15 may be constructed so that shaft 300 omits ribs 345 on its proximal end, and so that the installation tool 15 does not include handle assembly 500. In this case, pusher 400 may be moved proximally on shaft 300 by other means.

Figure 29:
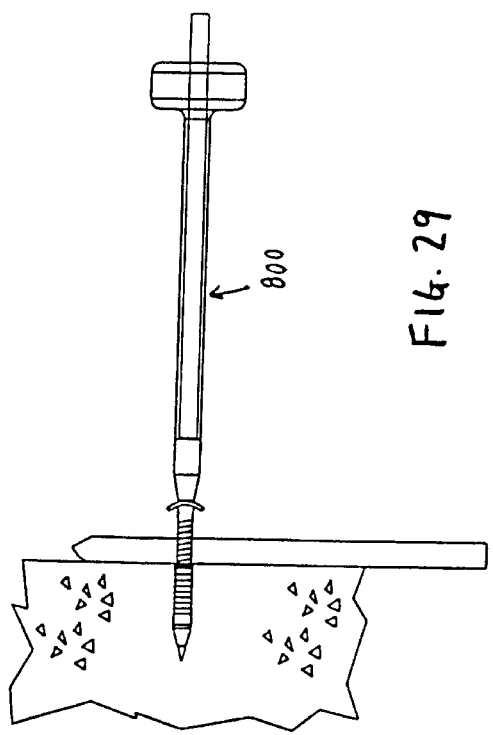
FIGS. 29 and 30 illustrate another preferred form of the novel fastening apparatus of the present invention being used to attach soft tissue (or the like) to bone.
Figure 30:
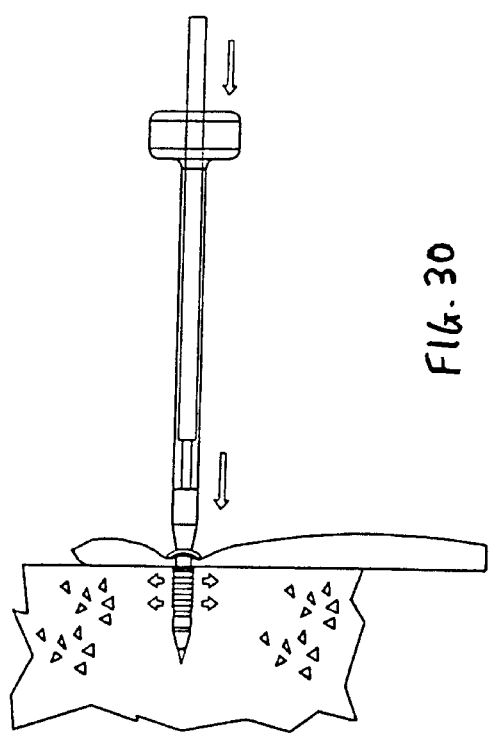

For example, and looking now at FIGS. 29 and 30, a cannulated driver 800, such as one having a so-called "slap hammer" configuration, can be used to drive pusher 400 distally on shaft 300, whereby to complete setting of fastener 10 in bone 700.

While the "slap hammer" construction shown in FIGS. 29 and 30 is simple and effective, it does suffer from the disadvantage that a proximally-directed counterforce is not being applied to expandable body 200 even as the distally-directed setting force is being applied to expander pin 300, as is the case with the use of handle assembly 500 described above.

It should be appreciated that, if desired, the expandable body's bone securement apparatus 150 (FIG. 12) may be omitted or, alternatively, replaced by a configuration different than the ribs 155 (FIG. 12) previously disclosed. By way of example but not limitation, bone securement apparatus 150 may comprise screw threads 155A shown in FIG. 31.

It should also be appreciated that, if desired, the expandable body's distal end 105 (FIG. 5) may have a configuration other than the smooth, frusto-conical one disclosed above. By way of example but not limitation, expandable body 100 may have screw threads formed on its tapered distal end. See, for example, FIG. 32, which shows the screw threads 110A formed on distal tip member 160.

Figure 34:
FIGS. 33–35 show details of an alternative form of the fastener's expander pin.
Figure 33:
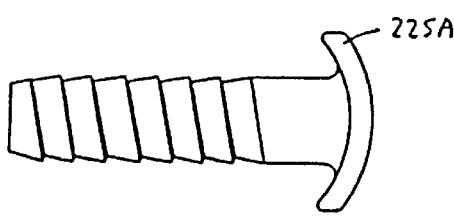
Figure 35:
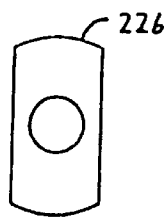

FIGS. 33–35 show an alternative form of expander pin 200. More particularly, the expander pin 200 shown in FIGS. 33–35 is similar to the expander pin 200 shown in FIGS. 14–16, except that with the expander pin of FIGS. 33–35, lateral projections 225A have their outlying edges 226 rounded into an arc-like configuration.

Figure 37:
FIGS. 36–38 show details of another alternative form of the fastener's expander pin.
Figure 36:
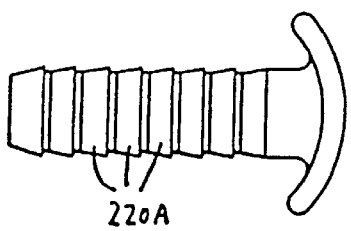
Figure 38:
Figure 19:
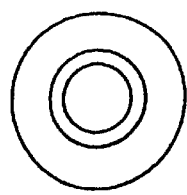
FIGS. 17–19 show details of the pusher member of the installation tool shown in FIG. 5.

FIGS. 36–38 show yet another alternative form of expander pin 200. More particularly, the expander pin 200 shown in FIGS. 36–38 is similar to the expander pin 200 shown in FIGS. 14–16, except that with the expander pin of FIGS. 36–38, fastener stabilization apparatus 215 comprises a plurality of frusto-conical ribs 220A, rather than the screw thread 220 shown in FIGS. 14–16.

It is also possible to form the fastener's tissue attachment apparatus 210 with a different configuration (and with a different manner of operation) than the tissue attachment apparatus shown in FIGS. 14–16 or 33–36.

More particularly, with the tissue attachment apparatus 210 shown in FIGS. 14–16 and 33–36, the tissue attachment apparatus essentially comprises a head for capturing the soft tissue to bone. However, it is also contemplated that tissue attachment apparatus 210 may comprise a suture-based mechanism for capturing the soft tissue to bone.

More particularly, and looking now at FIGS. 39–42, there is shown a fastener 10 in which tissue attachment apparatus 210 comprises a plurality of transverse bores 227 formed in expander pin 200 adjacent to its proximal end. Bores 227 accommodate one or more lengths of suture 228 (FIG. 39) which may be used to tie a piece of soft tissue (or the like) to bone. In one preferred form of the invention, expander pin 200 includes a cylindrical proximal end portion 229 (FIG. 40) having a diameter larger than the diameter of the central passageway 130 (FIG. 5) of expandable body 100, with transverse bores 227 being formed in cylindrical proximal end portion 229.

Figure 44:
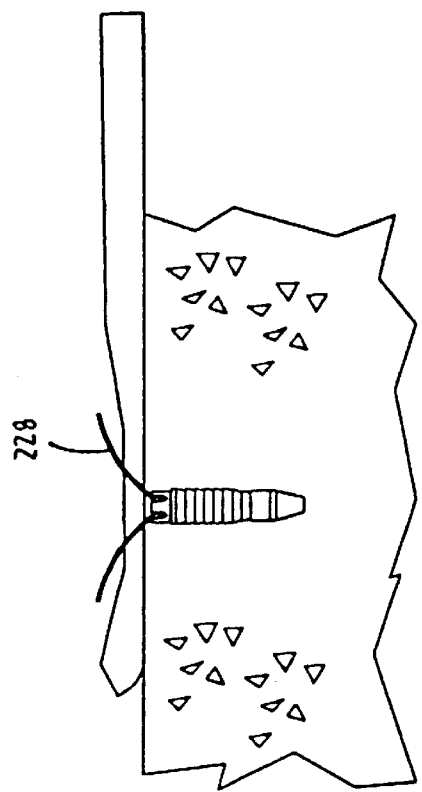
FIGS. 43 and 44 show the fastener of FIGS. 39–42 being used to attach soft tissue (or the like) to bone.
Figure 43:
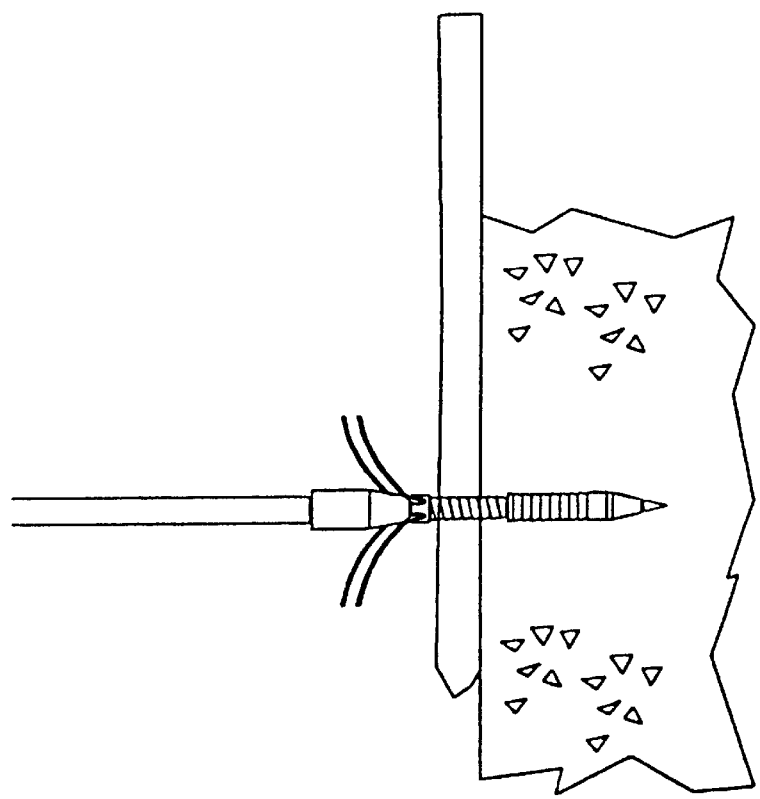

In use, the fastener is set through soft tissue 600 and into bone 700 in the normal manner (FIGS. 43 and 44); however, since the fastener lacks the lateral projections 225 (FIG. 14) previously disclosed, the proximal end of expander pin 200 will pass through soft tissue 600 without binding it to the bone (FIG. 44). However, sutures 228 will extend out of bone 700 and through soft tissue 600. As a result, these sutures may then be used to tie the soft tissue down to the bone.

If desired, the expander pin 200 shown in FIGS. 39–44 can be modified so as to have its fastener stabilization apparatus 215 in the form of ribs 220A (FIG. 45), rather than the screw thread 220 shown in FIG. 40.

With respect to the fastener configuration shown in FIGS. 39–45, it should be appreciated that by positioning transverse bores 227 (FIG. 40) in the diametrically-enlarged proximal end portion 229, the transverse bores 227 will remain proximal to expandable body 100 even after setting of the fastener (FIG. 44). As a result of this construction, sutures 228 will be able to slip within bores 227 even after fastener 10 has been completely deployed in bone 700. As will be apparent to persons skilled in the art, this can be advantageous in some circumstances during tissue fixation.

It is also possible to fabricate a fastener 10 with a suture-based mechanism for capturing soft tissue to bone, but where the sutures are prevented from slipping relative to the fastener once the fastener has been fully deployed in the bone.

More particularly, and looking now at FIGS. 46–49, there is shown a fastener 10 which includes an expander pin 200 having a plurality of transverse bores 227 intermediate its length (FIG. 47). Bores 227 accommodate the one or more lengths of suture 228 which may be used to tie a piece of soft tissue (or the like) to bone. In one preferred form of the invention, expander pin 200 includes a cylindrical intermediate portion 229A (FIG. 47) having a diameter substantially the same as the remainder of the expander pin, with transverse bores 227 being formed in the cylindrical intermediate portion 229A.

Looking next at FIGS. 50–53, in one preferred method of use, shaft 300 and expandable body 100 are driven into bone, and then a piece of suture 228 is looped around the soft tissue 600 which is to be attached to the bone 700 (FIG. 50). Then the suture 228 is pulled taut so as to bring the soft tissue into close proximity to the fastener (FIG. 51). Then pusher 400 is driven distally (FIG. 52) so as to completely set the fastener. At this point, since suture 228 is attached to expander pin 200 intermediate the length of the expander pin, the suture will be fixed in place relative to the deployed expander pin and, hence, will secure soft tissue 600 to bone 700. Installation tool 15 is then removed from the surgical site by unscrewing shaft 300 from expandable body 100 (FIG. 53).

If desired, expander pin 200 can also be formed so that its suture-receiving bores 227 are located adjacent to the distal end of the expander pin. For example., in another preferred form of the invention, expander pin 200 includes a cylindrical distal end portion 229B (FIG. 54) having a diameter substantially the same as the remainder of the expander pin, with transverse bores 227 being formed in the cylindrical distal end portion.

Figures 55, 56:
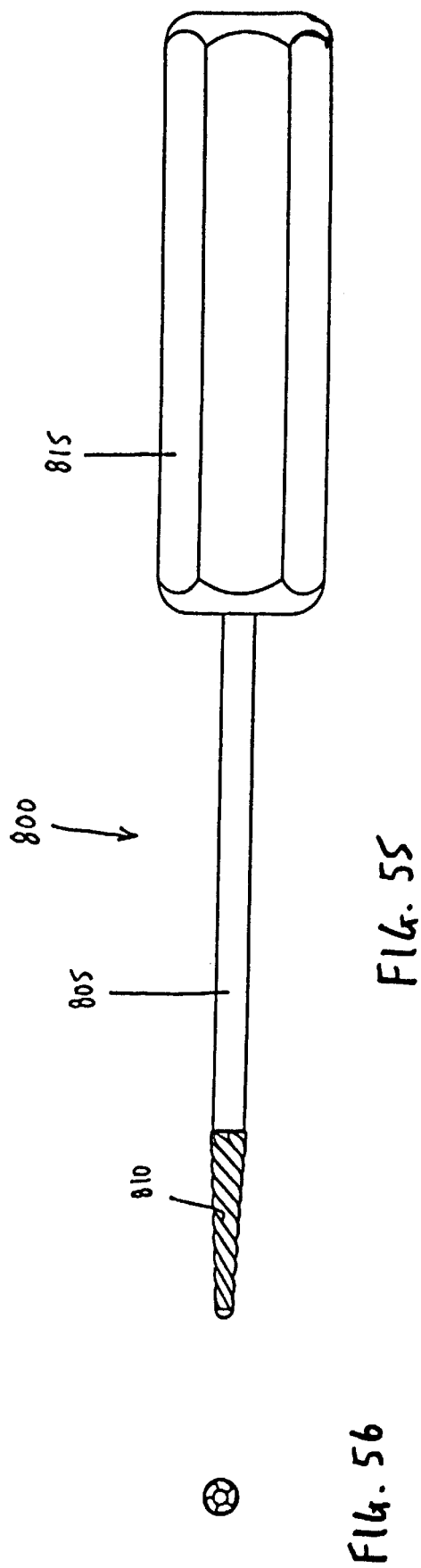
FIGS. 55 and 56 show details of a removal tool for removing a fastener formed and deployed in accordance with the present invention.

Looking next at FIGS. 55 and 56, there is shown a removal tool 800. Removal tool 800 can be used to remove a previously-deployed fastener 10, if the same should prove necessary or desirable. Removal tool 800 generally comprises a shaft 805 having a reverse thread 810 formed on its distal end and a handle 815 formed on its proximal end. The distal end of removal tool 800 is sized so as to be significantly larger than the longitudinal passageway 230 (FIG. 16) formed in expander pin 200.

When a previously-deployed fastener 10 is to be removed, the distal end of removal tool 800 is screwed into the proximal end of expander pin 200 using the removal tool's reverse screw thread 810. Inasmuch as the distal end of the removal tool is significantly larger than the longitudinal passageway 230 formed in expander pin 200, this action will cause the removal tool's distal threads 815 to force their way into the side wall of expander pin 200 and, depending on the sizing of the removal tool, possibly into the side wall of expandable body 100 as well. In any case, as the reverse thread 810 of the removal tool is screwed into the expander pin, continued reverse screwing will eventually cause the normally-threaded expander pin 200 to unscrew itself from expandable body 100. Removal tool 800 may then be used to remove expander pin 200 from expandable body 100. Expandable body 100 may then itself be removed from the surgical site by passing shaft 300 back into the interior of expandable body 100, screwing the shaft's threads 315 into the expandable body's threaded section 140, and then removing the shaft and expandable body from the bone.

What is claimed is:

1. Apparatus for attaching tissue to bone comprising:
    an expandable body configured to expand into bone, said expandable body defining a bore;
    an expander pin comprising a shaft sized to be received in the bore of said expandable body and expand said expandable body laterally when said expander pin is driven into said expandable body; and
    tissue attachment means associated with said shaft, said tissue attachment means having at least one laterally-extending projection for tacking tissue, and at least one distally-projecting longitudinal projection extending from said at least one laterally-extending projection;
    whereby when said expander pin is driven into said expandable body, said expandable body is attached to the bone and said tissue attachment means secures the tissue to said apparatus.

2. Apparatus according to claim 1 wherein said expander pin includes a fastener stabilization apparatus for stabilizing said expander pin relative to said expandable body.

3. Apparatus according to claim 2 wherein said fastener stabilization apparatus comprises threads.

4. Apparatus according to claim 2 wherein said fastener stabilization apparatus comprises ribs.

5. Apparatus according to claim 1 wherein said at least one laterally-extending projection has a substantially linear outer edge.

6. Apparatus according to claim 1 wherein said at least one laterally-extending projection has a substantially arc-like outer edge.

7. Apparatus according to claim 1 wherein said tissue attachment means comprises a bore formed in said expander pin and a suture extending through said expander pin bore.

8. Apparatus according to claim 7 wherein said tissue attachment means is configured so that said suture is slidable relative to said expander pin when said expander pin is received in said expandable body.

9. Apparatus according to claim 7 wherein said tissue attachment means further comprises a second bore formed in said expander pin and a second suture extending through said second expander pin bore.

10. Apparatus according to claim 1 wherein said expander pin has indicia for indicating depth.

11. Apparatus according to claim 1 wherein said expandable body is provided with a tapered distal end.

12. Apparatus according to claim 1 wherein said expandable body comprises a distal tip member and a proximal main member, said distal tip member being separable from said proximal main member.

13. Apparatus according to claim 12 wherein said distal tip member and said proximal main member are threadedly interengageable with one another.

14. Apparatus according to claim 12 wherein said distal tip member and said proximal main member are frictionally interengageable with one another.

15. Apparatus according to claim 12 wherein said expandable body distal tip member is tapered.

16. Apparatus according to claim 1 wherein said expandable body comprises a distal tip member constructed from a first material and a proximal main member constructed from a second material, and wherein said first material is harder than said second material.

17. Apparatus according to claim 1 wherein said expandable body includes bone securement apparatus for securing said expandable body relative to bone.

18. Apparatus according to claim 17 wherein said bone securement apparatus comprises ribs.

19. Apparatus according to claim 17 wherein said bone securement apparatus comprises threads.

20. Apparatus according to claim 1 wherein said apparatus further comprises an installation tool, and wherein said installation tool comprises a shaft sized to be slidingly received in said bore of said expandable body and a bore of said expander pin.

21. Apparatus according to claim 20 wherein said shaft is releasably attachable to said expandable body.

22. Apparatus according to claim 20 wherein said shaft and said expandable body are threadedly interengageable with one another.

23. Apparatus according to claim 20 wherein said shaft is provided with a tapered distal end.

24. Apparatus according to claim 20 wherein said shaft extends distally beyond said expandable body when said shaft is slidingly received in said bore of said expandable body.

25. Apparatus according to claim 20 wherein said apparatus further comprises a pusher member configured to drive said expander pin into said expandable body.

26. Apparatus according to claim 25 wherein said pusher member slides along said shaft when driving said expander pin into said expandable body.

27. Apparatus according to claim 1 wherein said apparatus further comprises a cannulated driver assembly adapted to drive said expander pin into said expandable body.

28. Apparatus according to claim 27 wherein said cannulated driver assembly slides along a shaft connected to said expandable body.

29. Apparatus according to claim 27 wherein said cannulated driver assembly includes a trigger for inducing the driving of said expander pin.

30. Apparatus according to claim 27 wherein said cannulated driver assembly comprises a slap hammer.

31. Apparatus for attaching tissue to bone comprising:

an expandable body configured to expand into bone, said expandable body defining a bore;

an expander pin comprising a shaft sized to be received in the bore of said expandable body and expand said expandable body laterally when said expander pin is driven into said expandable body; and tissue attachment means associated with said shaft;

whereby when said expander pin is driven into said expandable body, said expandable body is attached to the bone and said tissue attachment means secures the tissue to said apparatus;

wherein said expandable body comprises a distal tip member and a proximal main member, said distal tip member being separable from said proximal main member.

32. Apparatus for attaching tissue to bone comprising:

an expandable body configured to expand into bone, said expandable body defining a bore;

an expander pin comprising a shaft sized to be received in the bore of said expandable body and expand said expandable body laterally when said expander pin is driven into said expandable body; and tissue attachment means associated with said shaft;

whereby when said expander pin is driven into said expandable body, said expandable body is attached to the bone and said tissue attachment means secures the tissue to said apparatus;

wherein said expandable body comprises a distal tip member and a proximal main member, said distal tip member being separable from said proximal main member; and wherein said distal tip member and said proximal main member are threadedly interengageable with one another.

33. Apparatus for attaching tissue to bone comprising:

an expandable body configured to expand into bone, said expandable body defining a bore;

an expander pin comprising a shaft sized to be received in the bore of said expandable body and expand said expandable body laterally when said expander pin is driven into said expandable body; and tissue attachment means associated with said shaft;

whereby when said expander pin is driven into said expandable body, said expandable body is attached to the bone and said tissue attachment means secures the tissue to said apparatus;

wherein said expandable body comprises a distal tip member and a proximal main member, said distal tip member being separable from said proximal main member; and wherein said distal tip member and said proximal main member are frictionally interengageable with one another.

34. Apparatus for attaching tissue to bone comprising:

an expandable body configured to expand into bone, said expandable body defining a bore;

an expander pin comprising a shaft sized to be received in the bore of said expandable body and expand said expandable body laterally when said expander pin is driven into said expandable body; and tissue attachment means associated with said shaft;

whereby when said expander pin is driven into said expandable body, said expandable body is attached to the bone and said tissue attachment means secures the tissue to said apparatus;

wherein said expandable body comprises a distal tip member constructed from a first material and a proximal main member constructed from a second material, and wherein said first material is harder than said second material.

35. Apparatus for attaching tissue to bone comprising:

an expandable body configured to expand into bone, said expandable body defining a bore;

an expander pin comprising a shaft sized to be received in the bore of said expandable body and expand said expandable body laterally when said expander pin is driven into said expandable body; and tissue attachment means associated with said shaft;

whereby when said expander pin is driven into said expandable body, said expandable body is attached to the bone and said tissue attachment means secures the tissue to said apparatus;

wherein said expandable body comprises a distal tip member and a proximal main member, said distal tip member being separable from said proximal main member; and wherein said expandable body distal tip member is tapered.

36. Apparatus for attaching tissue to bone comprising:

an expandable body configured to expand into bone, said expandable body defining a bore;

an expander pin comprising a shaft sized to be received in the bore of said expandable body and expand said expandable body laterally when said expander pin is driven into said expandable body; and tissue attachment means associated with said shaft;

whereby when said expander pin is driven into said expandable body, said expandable body is attached to the bone and said tissue attachment means secures the tissue to said apparatus;

wherein said apparatus further comprises an installation tool, and wherein said installation tool comprises a shaft sized to be slidingly received in said bore of said expandable body and a bore of said expander pin.

37. Apparatus for attaching tissue to bone comprising:

an expandable body configured to expand into bone, said expandable body defining a bore;

an expander pin comprising a shaft sized to be received in the bore of said expandable body and expand said expandable body laterally when said expander pin is driven into said expandable body; and tissue attachment means associated with said shaft;

whereby when said expander pin is driven into said expandable body, said expandable body is attached to the bone and said tissue attachment means secures the tissue to said apparatus;

wherein said apparatus further comprises an installation tool, and wherein said installation tool comprises a shaft sized to be slidingly received in said bore of said expandable body and a bore of said expander pin; and wherein said shaft is releasably attachable to said expandable body.

38. Apparatus for attaching tissue to bone comprising:

an expandable body configured to expand into bone, said expandable body defining a bore;

an expander pin comprising a shaft sized to be received in the bore of said expandable body and expand said expandable body laterally when said expander pin is driven into said expandable body; and tissue attachment means associated with said shaft;

whereby when said expander pin is driven into said expandable body, said expandable body is attached to the bone and said tissue attachment means secures the tissue to said apparatus;

wherein said apparatus further comprises an installation tool, and wherein said installation tool comprises a shaft sized to be slidingly received in said bore of said expandable body and a bore of said expander pin; and wherein said shaft and said expandable body are threadedly interengageable with one another.

39. Apparatus for attaching tissue to bone comprising:

an expandable body configured to expand into bone, said expandable body defining a bore;

an expander pin comprising a shaft sized to be received in the bore of said expandable body and expand said expandable body laterally when said expander pin is driven into said expandable body; and tissue attachment means associated with said shaft;

whereby when said expander pin is driven into said expandable body, said expandable body is attached to the bone and said tissue attachment means secures the tissue to said apparatus;

wherein said apparatus further comprises an installation tool, and wherein said installation tool comprises a shaft sized to be slidingly received in said bore of said expandable body and a bore of said expander pin; and wherein said shaft is provided with a tapered distal end.

40. Apparatus for attaching tissue to bone comprising:

an expandable body configured to expand into bone, said expandable body defining a bore;

an expander pin comprising a shaft sized to be received in the bore of said expandable body and expand said expandable body laterally when said expander pin is driven into said expandable body; and tissue attachment means associated with said shaft;

whereby when said expander pin is driven into said expandable body, said expandable body is attached to the bone and said tissue attachment means secures the tissue to said apparatus;

wherein said apparatus further comprises an installation tool, and wherein said installation tool comprises a shaft sized to be slidingly received in said bore of said expandable body and a bore of said expander pin; and wherein said shaft extends distally beyond said expandable body when said shaft is slidingly received in said bore of said expandable body.

41. Apparatus for attaching tissue to bone comprising:

an expandable body configured to expand into bone, said expandable body defining a bore;

an expander pin comprising a shaft sized to be received in the bore of said expandable body and expand said expandable body laterally when said expander pin is driven into said expandable body; and tissue attachment means associated with said shaft;

whereby when said expander pin is driven into said expandable body, said expandable body is attached to the bone and said tissue attachment means secures the tissue to said apparatus;

wherein said apparatus further comprises an installation tool, and wherein said installation tool comprises a shaft sized to be slidingly received in said bore of said expandable body and a bore of said expander pin; and wherein said apparatus further comprises a pusher member configured to drive said expander pin into said expandable body.

42. Apparatus for attaching tissue to bone comprising:

an expandable body configured to expand into bone, said expandable body defining a bore;

an expander pin comprising a shaft sized to be received in the bore of said expandable body and expand said expandable body laterally when said expander pin is driven into said expandable body; and tissue attachment means associated with said shaft;

whereby when said expander pin is driven into said expandable body, said expandable body is attached to the bone and said tissue attachment means secures the tissue to said apparatus;

wherein said apparatus further comprises an installation tool, and wherein said installation tool comprises a shaft sized to be slidingly received in said bore of said expandable body and a bore of said expander pin; and wherein said apparatus further comprises a pusher member configured to drive said expander pin into said expandable body; and wherein said pusher member slides along said shaft when driving said expander pin into said expandable body.

43. Apparatus for attaching tissue to bone comprising:

an expandable body configured to expand into bone, said expandable body defining a bore;

an expander pin comprising a shaft sized to be received in the bore of said expandable body and expand said expandable body laterally when said expander pin is driven into said expandable body; and tissue attachment means associated with said shaft;

whereby when said expander pin is driven into said expandable body, said expandable body is attached to the bone and said tissue attachment means secures the tissue to -said apparatus;

wherein said apparatus further comprises a cannulated driver assembly adapted to drive said expander pin into said expandable body.

44. Apparatus for attaching tissue to bone comprising:

an expandable body configured to expand into bone, said expandable body defining a bore;

an expander pin comprising a shaft sized to be received in the bore of said expandable body and expand said expandable body laterally when said expander pin is driven into said expandable body; and tissue attachment means associated with said shaft;

whereby when said expander pin is driven into said expandable body, said expandable body is attached to the bone and said tissue attachment means secures the tissue to said apparatus;

wherein said apparatus further comprises an installation tool, and wherein said installation tool comprises a shaft sized to be slidingly received in said bore of said expandable body and a bore of said expander pin; and wherein said apparatus further comprises a cannulated driver assembly adapted to drive said expander pin into said expandable body; and wherein said cannulated driver assembly slides along a shaft connected to said expandable body.

45. Apparatus for attaching tissue to bone comprising:

an expandable body configured to expand into bone, said expandable body defining a bore;

an expander pin comprising a shaft sized to be received in the bore of said expandable body and expand said expandable body laterally when said expander pin is driven into said expandable body; and tissue attachment means associated with said shaft;

whereby when said expander pin is driven into said expandable body, said expandable body is attached to the bone and said tissue attachment means secures the tissue to said apparatus;

wherein said apparatus further comprises an installation tool, and wherein said installation tool comprises a shaft sized to be slidingly received in said bore of said expandable body and a bore of said expander pin; and wherein said apparatus further comprises a cannulated driver assembly adapted to drive said expander pin into said expandable body; and wherein said cannulated driver assembly includes a trigger for inducing the driving of said expander pin.

46. Apparatus for attaching tissue to bone comprising:

an expandable body configured to expand into bone, said expandable body defining a bore;

an expander pin comprising a shaft sized to be received in the bore of said expandable body and expand said expandable body laterally when said expander pin is driven into said expandable body; and tissue attachment means associated with said shaft;

whereby when said expander pin is driven into said expandable body, said expandable body is attached to the bone and said tissue attachment means secures the tissue to said apparatus;

wherein said apparatus further comprises an installation tool, and wherein said installation tool comprises a shaft sized to be slidingly received in said bore of said expandable body and a bore of said expander pin; and wherein said apparatus further comprises a cannulated driver assembly adapted to drive said expander pin into said expandable body; and wherein said cannulated driver assembly comprises a slap hammer.

47. Apparatus for attaching tissue to bone comprising:

an installation tool comprising a shaft having a distal end and a proximal end, said distal end of said shaft terminating in a relatively hard distal point;

an expandable body configured to expand into bone, said expandable body comprising a distal tip member and a proximal main member, said distal tip member being of harder material than said proximal main member, said distal tip member having a threaded recess in a proximal surface thereof and said proximal main member having a distally extending threaded projection threadedly interengageable with the threaded recess, and an opening extending from a distal end of said expandable body to a proximal end of said expandable body, said opening being sized to receive said shaft of said installation tool, and connecting apparatus for connecting said expandable body to said shaft of said installation tool when said distal end of said shaft of said installation tool protrudes from said distal end of said expandable body;

an expander pin comprising a shaft sized to be received in said opening in said expandable body and expand said expandable body radially when said expander pin is driven distally into said expandable body, and tissue attachment means associated with said shaft of said expander pin, said expander pin defining a bore sized to receive said shaft of said installation tool; and tissue attachment means associated with at least one of said expandable body and said expander pin;

whereby when said expander pin is driven into said expandable body, said expandable body will be attached to bone and said tissue attachment means will secure tissue to said apparatus.

48. Apparatus for attaching tissue to bone comprising:

a shaft;

an expandable body configured to expand into bone and comprising a distal tip member and a proximal main member, said distal tip member being of harder material than said proximal main member, said distal tip member having a threaded recess in a proximal surface thereof and said proximal main member having a distally extending threaded projection threadedly interengageable with the threaded recess, and said expandable body defining an opening, and said expandable body comprising connection apparatus for connecting said shaft to said expandable body;

an expander pin comprising a shaft sized to be received in said opening in said expandable body and expand said expandable body radially when said expander pin is driven into said expandable body; and tissue attachment apparatus associated with at least one of said expandable body and said expander pin;

whereby when said shaft is connected to said expandable body, and said expander pin is driven into said expandable body, said shaft can provide a counterforce to said expandable body so as to counteract the driving force applied to said expander pin.

49. Apparatus for attaching tissue to bone comprising:

an expandable body defining a bore and configured to expand into bone, said expandable body comprising a distal tip member and a proximal main member, said distal tip member being of harder material than said proximal main member, said distal tip member having a threaded recess in a proximal surface thereof and said proximal main member having a distally extending threaded projection threadedly interengageable with the threaded recess;

an expander pin comprising a shaft sized to be received in the bore of said expandable body and expand said expandable body laterally when said expander pin is driven into said expandable body; and tissue attachment means associated with said shaft;

whereby when said expander pin is driven into said expandable body, said expandable body is attached to the bone and said tissue attachment means secures the tissue to said apparatus.

50. Apparatus according to claim 49 wherein said expander pin includes a fastener stabilization apparatus for stabilizing said expander pin relative to said expandable body.

51. Apparatus according to claim 50 wherein said fastener stabilization apparatus comprises threads.

52. Apparatus according to claim 50 wherein said fastener stabilization apparatus comprises ribs.

53. Apparatus according to claim 49 wherein said tissue attachment means comprises at least one laterally-extending projection for tacking tissue.

54. Apparatus according to claim 53 wherein said at least one laterally-extending projection has a substantially linear outer edge.

55. Apparatus according to claim 53 wherein said at least one laterally-extending projection has a substantially arc-like outer edge.

56. Apparatus according to claim 53 wherein said at least one laterally-extending projection has a substantially convex configuration.

57. Apparatus according to claim 53 wherein said at least one laterally-extending projection has a substantially planar configuration.

58. Apparatus according to claim 53 wherein said at least one laterally-extending projection has a substantially concave configuration.

59. Apparatus according to claim 53 wherein said tissue attachment means further comprises at least one longitudinally-extending projection projecting distally out of said at least one laterally-extending projection.

60. Apparatus according to claim 49 wherein said tissue attachment means comprises a bore formed in said expander pin and a suture extending through said expander pin bore.

61. Apparatus according to claim 60 wherein said tissue attachment means is configured so that said suture may slide relative to said expander pin when said expander pin is received in said expandable body.

62. Apparatus according to claim 60 wherein said tissue attachment means further comprises a second bore formed in said expander pin and a second suture extending through said second expander pin bore.

63. Apparatus according to claim 49 wherein said expander pin has indicia for indicating depth.

64. Apparatus according to claim 49 wherein said expandable body distal tip is tapered.

65. Apparatus according to claim 49 wherein said expandable body includes bone securement apparatus for securing said expandable body relative to bone.

66. Apparatus according to claim 65 wherein said bone securement apparatus comprises ribs.

67. Apparatus according to claim 65 wherein said bone securement apparatus comprises threads.

68. Apparatus according to claim 49 wherein said apparatus further comprises an installation tool, and wherein said installation tool comprises a shaft sized to be slidingly received in said bore of said expandable body and in a bore of said expander pin.

69. Apparatus according to claim 68 wherein said shaft of said installation tool is releasably attachable to said expandable body.

70. Apparatus according to claim 68 wherein said shaft and said expandable body are threadingly interengageable with one another.

71. Apparatus according to claim 68 wherein said shaft has a tapered distal end.

72. Apparatus according to claim 68 wherein said shaft extends distally beyond said expandable body when said shaft is slidingly received in said bore of said expandable body.

73. Apparatus according to claim 68 wherein said apparatus further comprises a pusher member configured to drive said expander pin into said expandable body.

74. Apparatus according to claim 73 wherein said pusher member slides along said shaft of said installation tool when driving said expander pin into said expandable body.

75. Apparatus according to claim 49 wherein said apparatus further comprises a cannulated driver assembly adapted to drive said expander pin into said expandable body.

76. Apparatus according to claim 75, wherein said cannulated driver assembly slides along a shaft connected to said expandable body.

77. Apparatus according to claim 75 wherein said cannulated driver assembly includes a trigger for inducing the driving of said expander pin.

78. Apparatus according to claim 75 wherein said cannulated driver assembly comprises a slap hammer.

* * * * *